(12) United States Patent
Gelfand et al.

(10) Patent No.: US 8,735,085 B2
(45) Date of Patent: May 27, 2014

(54) METHOD FOR DIAGNOSING DISEASES USING A PROTEIN OR DEGRADATION PRODUCT BASED ON HALF-LIFE

(75) Inventors: Craig A. Gelfand, Jackson, NJ (US); Jizu Yi, Bayside, NY (US); Gang Ju, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 563 days.

(21) Appl. No.: 12/287,059

(22) Filed: Oct. 3, 2008

(65) Prior Publication Data

US 2009/0208923 A1 Aug. 20, 2009

Related U.S. Application Data

(60) Provisional application No. 60/977,980, filed on Oct. 5, 2007, provisional application No. 61/040,312, filed on Mar. 28, 2008.

(51) Int. Cl.
*C12Q 1/56* (2006.01)

(52) U.S. Cl.
USPC ............................................. 435/13; 435/4

(58) Field of Classification Search
USPC ....................................................... 435/4, 13
See application file for complete search history.

(56) References Cited

FOREIGN PATENT DOCUMENTS

| EP | 1619503 A1 | 1/2006 |
| WO | 2005/114222 A1 | 12/2005 |

OTHER PUBLICATIONS

Pool et al. "Biological half-life of transfused antihaemophilic globulin (factor VIII) in normal man", Brit. J. Haemat., 1967, 13:822-828.*
Scheja et al. "Von Willebrand factor propeptide as a marker of disease activity in systemic sclerosis" Arthrities Res. 2001, 3:178-182.*
Bond et al. "Evaluation of a finger prick blood collection method for the seroepidemiology of hepatitis B", Bulletin of the World Health Organization, 1978, 56(5):791-796.*
Marshall et al. "Processing of serum proteins underlines the mass spectral fingerprinting of myocardial infarction", Journal of Proteome Research, 2003, 2:361-372.*
Seino et al. "Application of NT-proBNP and BNP measurements in cardiac care: a more discerning marker for the detection and evaluation of heart failure", The European Journal of Heart Failure, 2004, 6:295-300.*
Gegenhuber et al. "Time course of B-type natriuretic peptide (BNP) and NT-proBNP changes in patients with decompensated heart failure", Clinical Chemistry, 2004, 50(2):454-456.*
Yi et al., J. Proteome Res. 2007, 6, 1768-1781.
Anderson et al., Mol. Cell. Proteomics 2002,1, 845-867.
Omenn et al.,. Proteomics 2005, 5, 3226-3245.
Adam et al., Cancer Res. 2002, 62, 3609-3614.
Petricoin et al., Urol. Oncol. 2001, 22, 322-8.
Ebert et al, J. Proteome Res. 2004, 3, 1261-1266.
Mor et al., Proc. Natl. Acad. Sci. USA 2005, 102, 7677-7682.
Irizarry, M. C,. NeuroRx 2004, 1, 226-234.
Petricoin et al., Lancet 2002, 359, 572-577.
Villanueva et al., J. Clin. Invest. 2006, 116, 271-284.
Moe, G. W., Curr. Opin. Cardiol. 2006, 21, 208-214.
Theodorescu et al., Lancet Oncol. 2006, 7, 230-240.
Ogata et al., J. Proteome Res. 2006, 5, 3318-25.
Ebert et al.,. J. Proteome Res. 2006, 5, 2152-2158.
Orvisky et al., Proteomics 2006, 6, 2895-902.
Marshall et al., J. Proteome Res. 2003, 2, 361-72.
Aebersold et al., J. Proteome Res. 2005, 4, 1104-1109.
Coombes et al., Nat. Biotechnol. 2005, 23, 291-292.
Check, Nature 2004, 429, 496-97.
Diamandis, J. Proteome Res. 2006, 5, 2079-82.
Flaig et al., J. Urol. 2007, 177, 1229-1237.
Tammen et al., Cancer Lett. 2007, 249, 80-86.
Lee et al., Adv. Cancer Res. 2007, 96, 269-298.
Rai et al., Proteomics 2005, 5, 3262-3277.
Banks et al., Clinical Chem. 2005, 51, 1637-49.
Hsieh et al., Proteomics 2006, 6, 3189-3198.
Walsh et al., Essays in Biochemistry 2002, 38, 95-111.
Gerber et al., PNAS 2003, 100, 6940-6945.
Kirkpatrick et al., Methods 2005, 35, 265-273.
Mayya et al., Mol. Cell. Proteomics 2005, 5, 1146-1157.
Zhang et al., J. Biomol. Tech. 2004, 15, 167-175.
Tholey et al., Anal. Chem. 2006, 78, 291-297.
Koomen et al., J. Proteome Res. 2005, 4, 972-981.
Oertel et al., Anal. Biochem. 2007, 367,152-8.
Willemse et al., Anal. Biochem. 2006, 356, 157-9.
Brun et al., Mol. Cell. Proteomics 2007, 6, 2139-49.
International Search Report and Written Opinion, PCT/US2008/011558, dated Feb. 9, 2009.
Hsieh Sen-Yung et al., 6(10); 3189-3198 (2006), XP002512353.

(Continued)

*Primary Examiner* — Bin Shen
(74) *Attorney, Agent, or Firm* — Lerner, David, Littenberg, Krumholz & Mentlik, LLP

(57) ABSTRACT

One aspect of the invention provides a method of diagnosing a disease condition, comprising measuring presence or amount of a targeted protein or a degradation product of said protein in a collected biological sample as a marker for the disease condition. The targeted protein or degradation product is selected for measurement based on a prior identification of a measurable half-life at a predetermined time period, including the time at which said method is conducted, and correlating said measuring with the presence or absence of the disease condition. The targeted protein or degradation product may be identified by selecting a protein known or suspected to be a diagnostic marker for the disease condition, analyzing degradation of the protein in the collected biological sample, and selecting a protein or degradation product that exhibits a measurable half-life at a predetermined period of time. The analyzing may include identifying degradation product(s) of the protein as a function of time, and half-life of the protein and the degradation product(s).

23 Claims, 9 Drawing Sheets

(56) References Cited

OTHER PUBLICATIONS

Database Biosis [Online] Biosciences Information Service, Philadelphia, PA, US; 1989, Meyer H G et al: "Development and Application of a Radioimmunoassay for Physostigmine" XP002512358 Database accession No. PREV199089030203 abstract.
Lucius et al., Biophysical Journal, 85(4); 2224-2239 (2003), XP002512355.
Zhou et al., The Journal of Physical Chemistry, 111(48); 13600-13610 (2007), XP002512356.
Yi et al., Journal of Proteome Research, 7(12); 5112-5118, (2008), XP002512357.
Karsan et al., Clinical Chemistry, 51(8); 1525-1528 (2005), XP002512354.

* cited by examiner

SMSR:    FPA → FPA-1 → FPA-2 → FPA-3 → FPA-4 → FPA-5 → FPA-6

| | FPA | FPA-1 | FPA-2 | FPA-3 | FPA-4 | FPA-5 |
|---|---|---|---|---|---|---|
| FG ($R^2$): | 0.84 | 0.78 | 0.77 | 0.87 | 0.76 | |
| $T_{1/2}$ (h): | 0.29 | 2.1 | 0.31 | 0.38 | 15.2 | |

SEQUENCE LISTING

<160> NUMBER OF SEQ ID NOS: 55

<210> SEQ ID NO 1
<211> LENGTH: 16
<212> TYPE: PRT
<213> ORGANISM: Homo sapiens

-continued

<400> SEQUENCE: 1

Ala Asp Ser Gly Glu Gly Asp Phe Leu Ala Glu Gly Gly Gly Val Arg
1               5                   10                  15

<210> SEQ ID NO 2
<211> LENGTH: 15
<212> TYPE: PRT
<213> ORGANISM: Homo sapiens

<400> SEQUENCE: 2

Asp Ser Gly Glu Gly Asp Phe Leu Ala Glu Gly Gly Gly Val Arg
1               5                   10                  15

<210> SEQ ID NO 3
<211> LENGTH: 14
<212> TYPE: PRT
<213> ORGANISM: Homo sapiens

<400> SEQUENCE: 3

Ser Gly Glu Gly Asp Phe Leu Ala Glu Gly Gly Gly Val Arg
1               5                   10

<210> SEQ ID NO 4
<211> LENGTH: 13
<212> TYPE: PRT
<213> ORGANISM: Homo sapiens

<400> SEQUENCE: 4

Gly Glu Gly Asp Phe Leu Ala Glu Gly Gly Gly Val Arg
1               5                   10

<210> SEQ ID NO 5
<211> LENGTH: 12
<212> TYPE: PRT
<213> ORGANISM: Homo sapiens

<400> SEQUENCE: 5

Glu Gly Asp Phe Leu Ala Glu Gly Gly Gly Val Arg
1               5                   10

<210> SEQ ID NO 6
<211> LENGTH: 11
<212> TYPE: PRT
<213> ORGANISM: Homo sapiens

<400> SEQUENCE: 6

Gly Asp Phe Leu Ala Glu Gly Gly Gly Val Arg
1               5                   10

<210> SEQ ID NO 7
<211> LENGTH: 10
<212> TYPE: PRT
<213> ORGANISM: Homo sapiens

<400> SEQUENCE: 7

Asp Phe Leu Ala Glu Gly Gly Gly Val Arg
1               5                   10

<210> SEQ ID NO 8
<211> LENGTH: 9
<212> TYPE: PRT
<213> ORGANISM: Homo sapiens

<400> SEQUENCE: 8

```
Phe Leu Ala Glu Gly Gly Gly Val Arg
1               5

<210> SEQ ID NO 9
<211> LENGTH: 8
<212> TYPE: PRT
<213> ORGANISM: Homo sapiens

<400> SEQUENCE: 9

Leu Ala Glu Gly Gly Gly Val Arg
1               5

<210> SEQ ID NO 10
<211> LENGTH: 29
<212> TYPE: PRT
<213> ORGANISM: Homo sapiens

<400> SEQUENCE: 10

Ser Ser Ser Tyr Ser Lys Gln Phe Thr Ser Ser Thr Ser Tyr Asn Arg
1               5                   10                  15

Gly Asp Ser Thr Phe Glu Ser Lys Ser Tyr Lys Met Ala
            20                  25

<210> SEQ ID NO 11
<211> LENGTH: 30
<212> TYPE: PRT
<213> ORGANISM: Homo sapiens

<400> SEQUENCE: 11

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser Tyr Lys Met Ala
            20                  25                  30

<210> SEQ ID NO 12
<211> LENGTH: 28
<212> TYPE: PRT
<213> ORGANISM: Homo sapiens

<400> SEQUENCE: 12

Ser Ser Ser Tyr Ser Lys Gln Phe Thr Ser Ser Thr Ser Tyr Asn Arg
1               5                   10                  15

Gly Asp Ser Thr Phe Glu Ser Lys Ser Tyr Lys Met
            20                  25

<210> SEQ ID NO 13
<211> LENGTH: 29
<212> TYPE: PRT
<213> ORGANISM: Homo sapiens

<400> SEQUENCE: 13

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser Tyr Lys Met
            20                  25

<210> SEQ ID NO 14
<211> LENGTH: 26
<212> TYPE: PRT
<213> ORGANISM: Homo sapiens

<400> SEQUENCE: 14

Ser Ser Ser Tyr Ser Lys Gln Phe Thr Ser Ser Thr Ser Tyr Asn Arg
1               5                   10                  15
```

Gly Asp Ser Thr Phe Glu Ser Lys Ser Tyr
            20                  25

<210> SEQ ID NO 15
<211> LENGTH: 27
<212> TYPE: PRT
<213> ORGANISM: Homo sapiens

<400> SEQUENCE: 15

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser Tyr
            20                  25

<210> SEQ ID NO 16
<211> LENGTH: 25
<212> TYPE: PRT
<213> ORGANISM: Homo sapiens

<400> SEQUENCE: 16

Ser Ser Ser Tyr Ser Lys Gln Phe Thr Ser Thr Ser Tyr Asn Arg
1               5                   10                  15

Gly Asp Ser Thr Phe Glu Ser Lys Ser
            20                  25

<210> SEQ ID NO 17
<211> LENGTH: 26
<212> TYPE: PRT
<213> ORGANISM: Homo sapiens

<400> SEQUENCE: 17

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser
            20                  25

<210> SEQ ID NO 18
<211> LENGTH: 23
<212> TYPE: PRT
<213> ORGANISM: Homo sapiens

<400> SEQUENCE: 18

Ser Ser Ser Tyr Ser Lys Gln Phe Thr Ser Thr Ser Tyr Asn Arg
1               5                   10                  15

Gly Asp Ser Thr Phe Glu Ser
            20

<210> SEQ ID NO 19
<211> LENGTH: 24
<212> TYPE: PRT
<213> ORGANISM: Homo sapiens

<400> SEQUENCE: 19

Lys Ser Ser Ser Tyr Ser Lys Gln Phe Thr Ser Thr Ser Tyr Asn
1               5                   10                  15

Arg Gly Asp Ser Thr Phe Glu Ser
            20

<210> SEQ ID NO 20
<211> LENGTH: 21
<212> TYPE: PRT
<213> ORGANISM: Homo sapiens

```
<400> SEQUENCE: 20

Ser Ser Tyr Ser Lys Gln Phe Thr Ser Ser Thr Ser Tyr Asn Arg Gly
1               5                   10                  15

Asp Ser Thr Phe Glu
            20

<210> SEQ ID NO 21
<211> LENGTH: 17
<212> TYPE: PRT
<213> ORGANISM: Homo sapiens

<400> SEQUENCE: 21

Ser Ser Lys Ile Thr His Arg Ile His Trp Glu Ser Ala Ser Leu Leu
1               5                   10                  15

Arg

<210> SEQ ID NO 22
<211> LENGTH: 16
<212> TYPE: PRT
<213> ORGANISM: Homo sapiens

<400> SEQUENCE: 22

Ser Ser Lys Ile Thr His Arg Ile His Trp Glu Ser Ala Ser Leu Leu
1               5                   10                  15

<210> SEQ ID NO 23
<211> LENGTH: 15
<212> TYPE: PRT
<213> ORGANISM: Homo sapiens

<400> SEQUENCE: 23

Ser Lys Ile Thr His Arg Ile His Trp Glu Ser Ala Ser Leu Leu
1               5                   10                  15

<210> SEQ ID NO 24
<211> LENGTH: 14
<212> TYPE: PRT
<213> ORGANISM: Homo sapiens

<400> SEQUENCE: 24

Lys Ile Thr His Arg Ile His Trp Glu Ser Ala Ser Leu Leu
1               5                   10

<210> SEQ ID NO 25
<211> LENGTH: 13
<212> TYPE: PRT
<213> ORGANISM: Homo sapiens

<400> SEQUENCE: 25

Ile Thr His Arg Ile His Trp Glu Ser Ala Ser Leu Leu
1               5                   10

<210> SEQ ID NO 26
<211> LENGTH: 12
<212> TYPE: PRT
<213> ORGANISM: Homo sapiens

<400> SEQUENCE: 26

Thr His Arg Ile His Trp Glu Ser Ala Ser Leu Leu
1               5                   10

<210> SEQ ID NO 27
<211> LENGTH: 11
<212> TYPE: PRT
```

-continued

<213> ORGANISM: Homo sapiens

<400> SEQUENCE: 27

His Arg Ile His Trp Glu Ser Ala Ser Leu Leu
1               5                   10

<210> SEQ ID NO 28
<211> LENGTH: 10
<212> TYPE: PRT
<213> ORGANISM: Homo sapiens

<400> SEQUENCE: 28

Arg Ile His Trp Glu Ser Ala Ser Leu Leu
1               5                   10

<210> SEQ ID NO 29
<211> LENGTH: 9
<212> TYPE: PRT
<213> ORGANISM: Homo sapiens

<400> SEQUENCE: 29

Ile His Trp Glu Ser Ala Ser Leu Leu
1               5

<210> SEQ ID NO 30
<211> LENGTH: 8
<212> TYPE: PRT
<213> ORGANISM: Homo sapiens

<400> SEQUENCE: 30

His Trp Glu Ser Ala Ser Leu Leu
1               5

<210> SEQ ID NO 31
<211> LENGTH: 15
<212> TYPE: PRT
<213> ORGANISM: Homo sapiens

<400> SEQUENCE: 31

Ser Ser Lys Ile Thr His Arg Ile His Trp Glu Ser Ala Ser Leu
1               5                   10                  15

<210> SEQ ID NO 32
<211> LENGTH: 16
<212> TYPE: PRT
<213> ORGANISM: Homo sapiens

<400> SEQUENCE: 32

Arg Asn Gly Phe Lys Ser His Ala Leu Gln Leu Asn Asn Arg Gln Ile
1               5                   10                  15

<210> SEQ ID NO 33
<211> LENGTH: 17
<212> TYPE: PRT
<213> ORGANISM: Homo sapiens

<400> SEQUENCE: 33

Arg Asn Gly Phe Lys Ser His Ala Leu Gln Leu Asn Asn Arg Gln Ile
1               5                   10                  15
Arg

<210> SEQ ID NO 34
<211> LENGTH: 15
<212> TYPE: PRT
<213> ORGANISM: Homo sapiens

<400> SEQUENCE: 34

Asn Gly Phe Lys Ser His Ala Leu Gln Leu Asn Asn Arg Gln Ile
1               5                   10                  15

<210> SEQ ID NO 35
<211> LENGTH: 16
<212> TYPE: PRT
<213> ORGANISM: Homo sapiens

<400> SEQUENCE: 35

Asn Gly Phe Lys Ser His Ala Leu Gln Leu Asn Asn Arg Gln Ile Arg
1               5                   10                  15

<210> SEQ ID NO 36
<211> LENGTH: 14
<212> TYPE: PRT
<213> ORGANISM: Homo sapiens

<400> SEQUENCE: 36

Asn Gly Phe Lys Ser His Ala Leu Gln Leu Asn Asn Arg Gln
1               5                   10

<210> SEQ ID NO 37
<211> LENGTH: 13
<212> TYPE: PRT
<213> ORGANISM: Homo sapiens

<400> SEQUENCE: 37

Asn Gly Phe Lys Ser His Ala Leu Gln Leu Asn Asn Arg
1               5                   10

<210> SEQ ID NO 38
<211> LENGTH: 30
<212> TYPE: PRT
<213> ORGANISM: Homo sapiens

<400> SEQUENCE: 38

Gly Leu Glu Glu Glu Leu Gln Phe Ser Leu Gly Ser Lys Ile Asn Val
1               5                   10                  15

Lys Val Gly Gly Asn Ser Lys Gly Thr Leu Lys Val Leu Arg
            20                  25                  30

<210> SEQ ID NO 39
<211> LENGTH: 31
<212> TYPE: PRT
<213> ORGANISM: Homo sapiens

<400> SEQUENCE: 39

Arg Gly Leu Glu Glu Glu Leu Gln Phe Ser Leu Gly Ser Lys Ile Asn
1               5                   10                  15

Val Lys Val Gly Gly Asn Ser Lys Gly Thr Leu Lys Val Leu Arg
            20                  25                  30

<210> SEQ ID NO 40
<211> LENGTH: 26
<212> TYPE: PRT
<213> ORGANISM: Homo sapiens

<400> SEQUENCE: 40

Gly Leu Glu Glu Glu Leu Gln Phe Ser Leu Gly Ser Lys Ile Asn Val
1               5                   10                  15

Lys Val Gly Gly Asn Ser Lys Gly Thr Leu
            20                  25

```
<210> SEQ ID NO 41
<211> LENGTH: 27
<212> TYPE: PRT
<213> ORGANISM: Homo sapiens

<400> SEQUENCE: 41

Arg Gly Leu Glu Glu Glu Leu Gln Phe Ser Leu Gly Ser Lys Ile Asn
1               5                   10                  15

Val Lys Val Gly Gly Asn Ser Lys Gly Thr Leu
            20                  25

<210> SEQ ID NO 42
<211> LENGTH: 22
<212> TYPE: PRT
<213> ORGANISM: Homo sapiens

<400> SEQUENCE: 42

Gly Leu Glu Glu Glu Leu Gln Phe Ser Leu Gly Ser Lys Ile Asn Val
1               5                   10                  15

Lys Val Gly Gly Asn Ser
            20

<210> SEQ ID NO 43
<211> LENGTH: 23
<212> TYPE: PRT
<213> ORGANISM: Homo sapiens

<400> SEQUENCE: 43

Arg Gly Leu Glu Glu Glu Leu Gln Phe Ser Leu Gly Ser Lys Ile Asn
1               5                   10                  15

Val Lys Val Gly Gly Asn Ser
            20

<210> SEQ ID NO 44
<211> LENGTH: 17
<212> TYPE: PRT
<213> ORGANISM: Homo sapiens

<400> SEQUENCE: 44

Gly Leu Glu Glu Glu Leu Gln Phe Ser Leu Gly Ser Lys Ile Asn Val
1               5                   10                  15

Arg

<210> SEQ ID NO 45
<211> LENGTH: 18
<212> TYPE: PRT
<213> ORGANISM: Homo sapiens

<400> SEQUENCE: 45

Arg Gly Leu Glu Glu Glu Leu Gln Phe Ser Leu Gly Ser Lys Ile Asn
1               5                   10                  15

Val Arg

<210> SEQ ID NO 46
<211> LENGTH: 38
<212> TYPE: PRT
<213> ORGANISM: Homo sapiens

<400> SEQUENCE: 46

Gln Ala Gly Ala Ala Gly Ser Arg Met Asn Phe Arg Pro Gly Val Leu
1               5                   10                  15
```

```
Ser Ser Arg Gln Leu Gly Leu Pro Gly Pro Pro Asp Val Pro Asp His
            20                  25                  30

Ala Ala Tyr His Pro Phe
            35

<210> SEQ ID NO 47
<211> LENGTH: 39
<212> TYPE: PRT
<213> ORGANISM: Homo sapiens

<400> SEQUENCE: 47

Arg Gln Ala Gly Ala Ala Gly Ser Arg Met Asn Phe Arg Pro Gly Val
1               5                   10                  15

Leu Ser Ser Arg Gln Leu Gly Leu Pro Gly Pro Pro Asp Val Pro Asp
            20                  25                  30

His Ala Ala Tyr His Pro Phe
            35

<210> SEQ ID NO 48
<211> LENGTH: 30
<212> TYPE: PRT
<213> ORGANISM: Homo sapiens

<400> SEQUENCE: 48

Met Asn Phe Arg Pro Gly Val Leu Ser Ser Arg Gln Leu Gly Leu Pro
1               5                   10                  15

Gly Pro Pro Asp Val Pro Asp His Ala Ala Tyr His Pro Phe
            20                  25                  30

<210> SEQ ID NO 49
<211> LENGTH: 26
<212> TYPE: PRT
<213> ORGANISM: Homo sapiens

<400> SEQUENCE: 49

Pro Gly Val Leu Ser Ser Arg Gln Leu Gly Leu Pro Gly Pro Pro Asp
1               5                   10                  15

Val Pro Asp His Ala Ala Tyr His Pro Phe
            20                  25

<210> SEQ ID NO 50
<211> LENGTH: 25
<212> TYPE: PRT
<213> ORGANISM: Homo sapiens

<400> SEQUENCE: 50

Gly Val Leu Ser Ser Arg Gln Leu Gly Leu Pro Gly Pro Pro Asp Val
1               5                   10                  15

Pro Asp His Ala Ala Tyr His Pro Phe
            20                  25

<210> SEQ ID NO 51
<211> LENGTH: 22
<212> TYPE: PRT
<213> ORGANISM: Homo sapiens

<400> SEQUENCE: 51

Ser Ser Arg Gln Leu Gly Leu Pro Gly Pro Pro Asp Val Pro Asp His
1               5                   10                  15

Ala Ala Tyr His Pro Phe
            20
```

-continued

```
<210> SEQ ID NO 52
<211> LENGTH: 21
<212> TYPE: PRT
<213> ORGANISM: Homo sapiens

<400> SEQUENCE: 52

Ser Arg Gln Leu Gly Leu Pro Gly Pro Pro Asp Val Pro Asp His Ala
1               5                   10                  15

Ala Tyr His Pro Phe
            20

<210> SEQ ID NO 53
<211> LENGTH: 19
<212> TYPE: PRT
<213> ORGANISM: Homo sapiens

<400> SEQUENCE: 53

Gln Leu Gly Leu Pro Gly Pro Pro Asp Val Pro Asp His Ala Ala Tyr
1               5                   10                  15

His Pro Phe

<210> SEQ ID NO 54
<211> LENGTH: 17
<212> TYPE: PRT
<213> ORGANISM: Homo sapiens

<400> SEQUENCE: 54

Gly Leu Pro Gly Pro Pro Asp Val Pro Asp His Ala Ala Tyr His Pro
1               5                   10                  15

Phe

<210> SEQ ID NO 55
<211> LENGTH: 7
<212> TYPE: PRT
<213> ORGANISM: Homo sapiens

<400> SEQUENCE: 55

His Ala Ala Tyr His Pro Phe
1               5
```

US 8,735,085 B2

METHOD FOR DIAGNOSING DISEASES USING A PROTEIN OR DEGRADATION PRODUCT BASED ON HALF-LIFE

CROSS-REFERENCE TO RELATED APPLICATIONS

This application claims the benefit of the filing dates of U.S. Provisional Patent Application No. 60/977,980 filed Oct. 5, 2007, and U.S. Provisional Patent Application No. 61/040, 312 filed Mar. 28, 2008 the disclosures of which are hereby incorporated herein by reference.

BACKGROUND OF THE INVENTION

Human blood serum and plasma contain a wealth of information relating to disease status and have received significant attention as a source of potential diagnostic markers, especially within the last decade (1, 2). Biomarkers include a broad spectrum of proteins (3-7) and peptides (8-10). One such peptide found in blood is fibrinogen peptide A (fibrinopeptide A or FPA), the level of which has been correlated to several diseases including urothelial cancer (11), ovarian cancer (12), gastric cancer (13), and hepatocellular carcinoma (14). The discovery of disease markers in blood fluid continues to accelerate as proteomics technology becomes both more powerful and more widely available (16-17).

Preanalytical variability is a particularly complex issue in protein biomarker discovery, especially with blood samples (24-26). A freshly drawn blood sample is a living tissue, filled with a wide range of naturally active and ex vivo activated biochemical pathways, which may alter or destroy protein and peptide content in the sample. Some of the blood enzymes (e.g., proteases) are known to be involved in biochemical processes, such as the protease cascade responsible for coagulation (27). The functions of other enzymes remain to be elucidated.

Currently, a simple, cost-effective, reproducible and accurate method of measuring the information in human serum and plasma is desired. Additionally, a method of using the discovery of markers in bodily fluids, especially blood fluid, to more accurately diagnose prognostic conditions and disease status is desired.

SUMMARY OF THE INVENTION

One aspect of the present invention provides a method of diagnosing a disease or other pathological or abnormal condition, comprising measuring presence or amount of a targeted protein (peptide) or a degradation product of the protein in a collected biological sample as a marker for the disease condition. The targeted protein or its degradation product(s) is selected for measurement based on a prior identification of a measurable half-life at a predetermined time period, including the time at which the method is conducted, and correlating the measuring with the presence or absence of the disease condition. The targeted protein or degradation product may be identified by selecting a protein known or suspected to be a diagnostic biomarker for the disease condition, analyzing degradation of the peptide in the collected biological sample, and selecting a peptide or its degradation product that exhibits a measurable half-life at a predetermined period of time. The analyzing may include identifying degradation product(s) of the protein (or peptide) as a function of time, and measuring half-life of the peptide and its degradation product(s).

Another aspect of the present invention provides a method of identifying a protein (or peptide) and/or its degradation product thereof as a marker for a disease or other pathological or abnormal condition, comprising selecting a protein known or suspected to be a diagnostic marker for the disease condition, analyzing degradation of the protein in the collected biological sample, comprising identifying degradation product(s) of the protein as a function of time and half-life of the protein and the degradation product(s), and selecting a protein or degradation product that exhibits a measurable half-life at a predetermined period of time.

Yet another aspect of the invention provides a computer-readable medium storing a computer-readable program, the program being operable to perform a method for determining a protein or degradation product thereof for diagnosing a disease or other pathological or abnormal condition. The method performed by the program may include analyzing degradation of the protein in the collected biological sample, comprising identifying degradation product(s) of the protein as a function of time and half-life of the protein and the degradation product(s), and selecting a protein or degradation product that exhibits a measurable half-life at a predetermined period of time.

To diagnose diseases or other pathological or abnormal conditions, physicians, nurses, phlebotomists, and other medical practitioners may take a biological sample from a patient, such as a blood sample, for analysis. This sample contains proteins or peptides, the presence of amount of which in some circumstances may indicate the presence or severity of a disease or pathological condition of the patient. However, these proteins or peptides, which are commonly referred to as diagnostic markers or biomarkers, are susceptible to degradation substantially simultaneously withdrawal of the blood sample into or on a collection vehicle, to the point that the marker might not be present in detectable quantities by the time the sample is actually analyzed. Thus, the present invention provides a solution to the problem by a diagnostic method which includes a prior recognition of when or how long the marker possesses a measurable half-life upon storage, an identification of the protein or peptide fragments of the marker that are produced as a result of the degradation process, and a recognition of each of their respective half-lives. In so doing, the present method enables a person of skill in the art to select for measurement either the marker or one of its degradation products that has a half-life at a predetermined time period, such as the time at which analysis of the sample is conducted. Thus, an advantage of the present invention will avoid false negative results associated with diagnostic assays based on identification of diagnostic protein or peptide markers.

Another underlying discovery upon which the present invention is based is that the degradation profile, and particularly the half-lives of a diagnostic marker and its degradation products, are not only a function of time, but a function of the chemical constituency of the vehicle (or collection environment) in which it is collected. As explained in detail in the present specification, the half-life of a diagnostic protein or peptide marker measured in blood samples collected in vehicles such as containers containing the anti-coagulants EDTA, citrate and heparin respectively, or a mixture of protease inhibitors, will all differ. Accordingly, a feature of the present invention is that the prior recognition of the half-life of the marker and its degradation products, and the diagnostic method itself, are conducted using a collection vehicle with the same or at least functionally equivalent chemical constituency.

BRIEF DESCRIPTION OF THE DRAWINGS

FIG. 4A is a summary of modeling results of multiple step degradations of FPA peptide.

DETAILED DESCRIPTION

In this application, the word "marker", "biomarker", "analyte" and similar words are used essentially interchangeably, referring to the protein or peptide, or degradation products thereof, and the associated implication of measuring the level and/or presence/absence of said protein or peptide as part of the diagnostic process. Furthermore, the words protein and peptide are used interchangeably.

The term "protein", as used herein, means any protein, including but not limited to peptides, polypeptides, protein complexes, intact proteins, glycoproteins, etc.

A targeted protein or degradation product thereof may be measured in a collected biological sample, and the presence or absence of such protein or degradation product may be correlated with the presence or absence of a disease condition. For example, biomarkers of prostate, bladder, and/or breast cancer include blood coagulation proteins and peptides such as FPA, Fibrinogen α and the coagulation factors, components of the complement system including C3f and C4a, and a wide variety of other proteins including ITIH4, apoA-I, apoA-IV, apoE, Clusterin, Bradykinin, Kininogen HMW, and Transthyretin.

The targeted protein and degradation products may be identified by selecting a known or suspected biomarker, and analyzing its degradation as a function of time. This analysis includes identifying the degradation products of the marker, and further identifying the half-lives of the markers. Thus, it may be determined which degradation product(s) will exist in a measurable quantity at a predetermined period of time, and such degradation product(s) may be targeted for measurement. A method of identifying targeted proteins or degradation products thereof, according to an aspect of the invention, is provided below.

Figure 1:
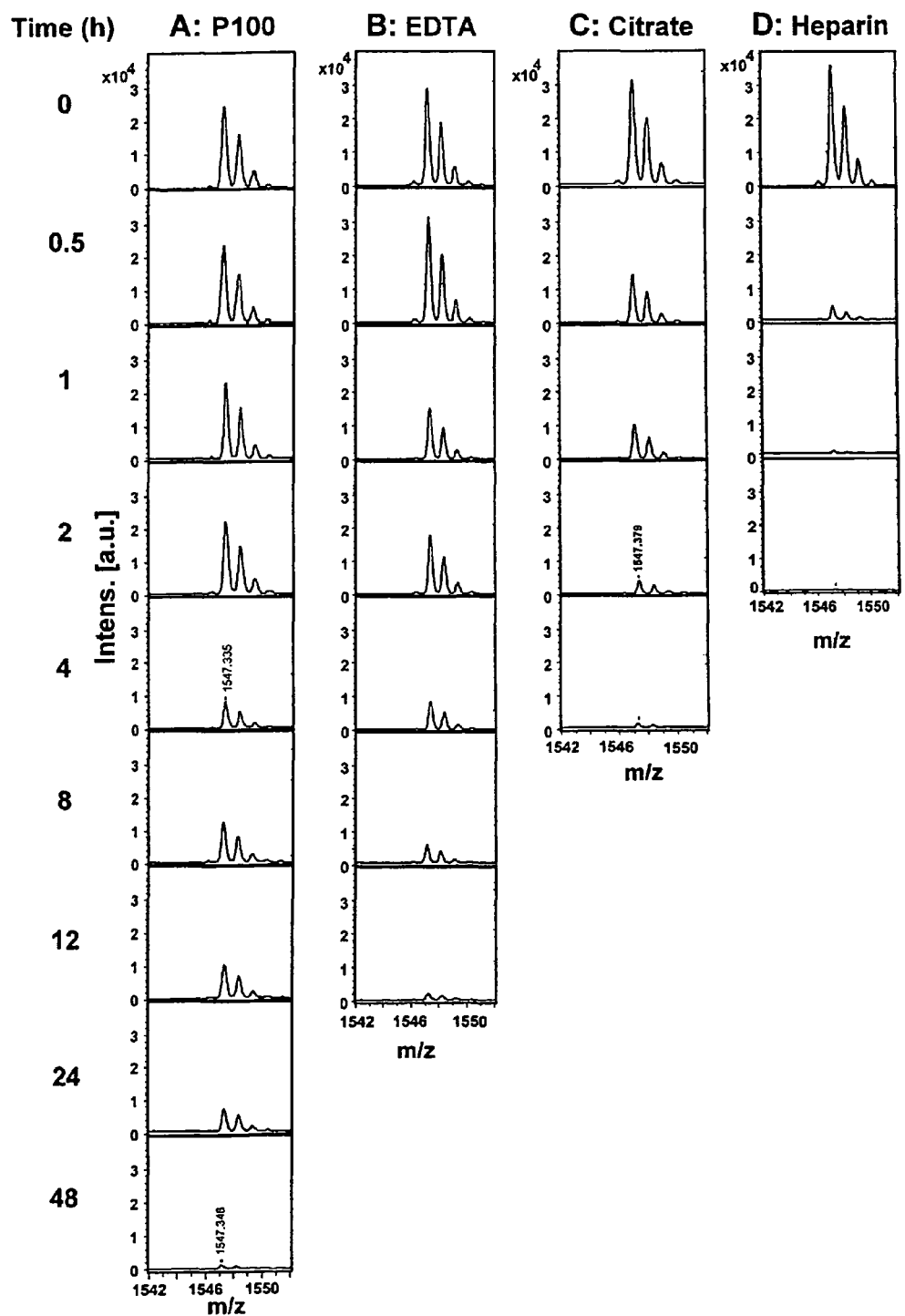
FIG. 1 is a graphical representation of the intensities of FPA over time in various plasma samples.

One example of a diagnostic marker that displays the above behavior is fibrinogen peptide A (FPA). FPA is the primary peptide resulting from thrombin cleaving fibrinogen, which is the final biologically process leading to fibrin aggregation into the protein network that forms the structure of a blood clot. In addition to reflecting clot formation, measurement of FPA levels has been implicated as having potential diagnostic utility for various cancers (11-14). FIG. 1 shows the intensity of FPA in various plasma samples stored in different collection vehicles, namely blood collection tubes. The four blood collection tubes represented in this figure relate to a blood collection tube with a protease inhibitor mixture (P100 blood collection tube from Becton Dickinson & Co., Franklin Lakes, N.J. Catalog #366456), a blood collection tube with an EDTA anticoagulant (EDTA blood collection tube from Becton Dickinson & Co., Franklin Lakes, N.J. Catalog #367525), a blood collection tube with a citrate anticoagulant (citrate blood collection tube from Becton Dickinson & Co., Franklin Lakes, N.J. Catalog #369714), and finally a blood collection tube with a heparin anticoagulant (heparin blood collection tube from Becton Dickinson & Co., Franklin Lakes, N.J. Catalog #367886). A separate illustration of the measured intensities for FPA at different periods of time until the FPA is undetectable is also represented in FIG. 1. As shown, the detected intensity or presence of FPA in each plasma sample decreases significantly over time. In the heparin tube for example, the FPA is undetectable in less than two hours after collection of the original sample.

FPA degrades less rapidly in alternative blood sample types. For example, as further shown in FIG. 2, a detectable intensity of FPA remains in the EDTA and the P100 tubes for a much longer period of time. However, while the FPA degrades somewhat less rapidly in the other samples, it is still only detectable up until a period of time approximately 12-48 hours after collection. In practice, clinical tests are ordered, collected, processed, and analyzed with different degrees of urgency and priority. This results in some tests being processed within minutes or hours, e.g., in a hospital setting, while other tests may be tested on the order of hours to days after the time of collection, e.g., a sample drawn in a private physician office and shipped for subsequent processing in a centralized testing laboratory. Furthermore, in many laboratories, samples are retained in refrigerators for up to a week or more, in case subsequent testing or retesting needs to be performed on the original sample. In some settings, it is not uncommon for clinical analysis of samples to be performed 48 hours or more after sample collection. Thus, under ordinary circumstances, FPA, as illustrated in FIG. 1, may degrade to very low or undetectable levels, which are certainly not representative of the original level in the fresh sample at or soon after collection. As a result, the ability to provide a physician with accurate and reliable diagnostic information resulting from the analysis of certain degradable analytes may be jeopardized. Specifically, the presence, absence, or level of presence for an analyte of interest may not be in all cases reliably depended upon given that the relevant marker of that condition was degraded to negligible (undetectable) levels before analysis was performed.

Figure 3:
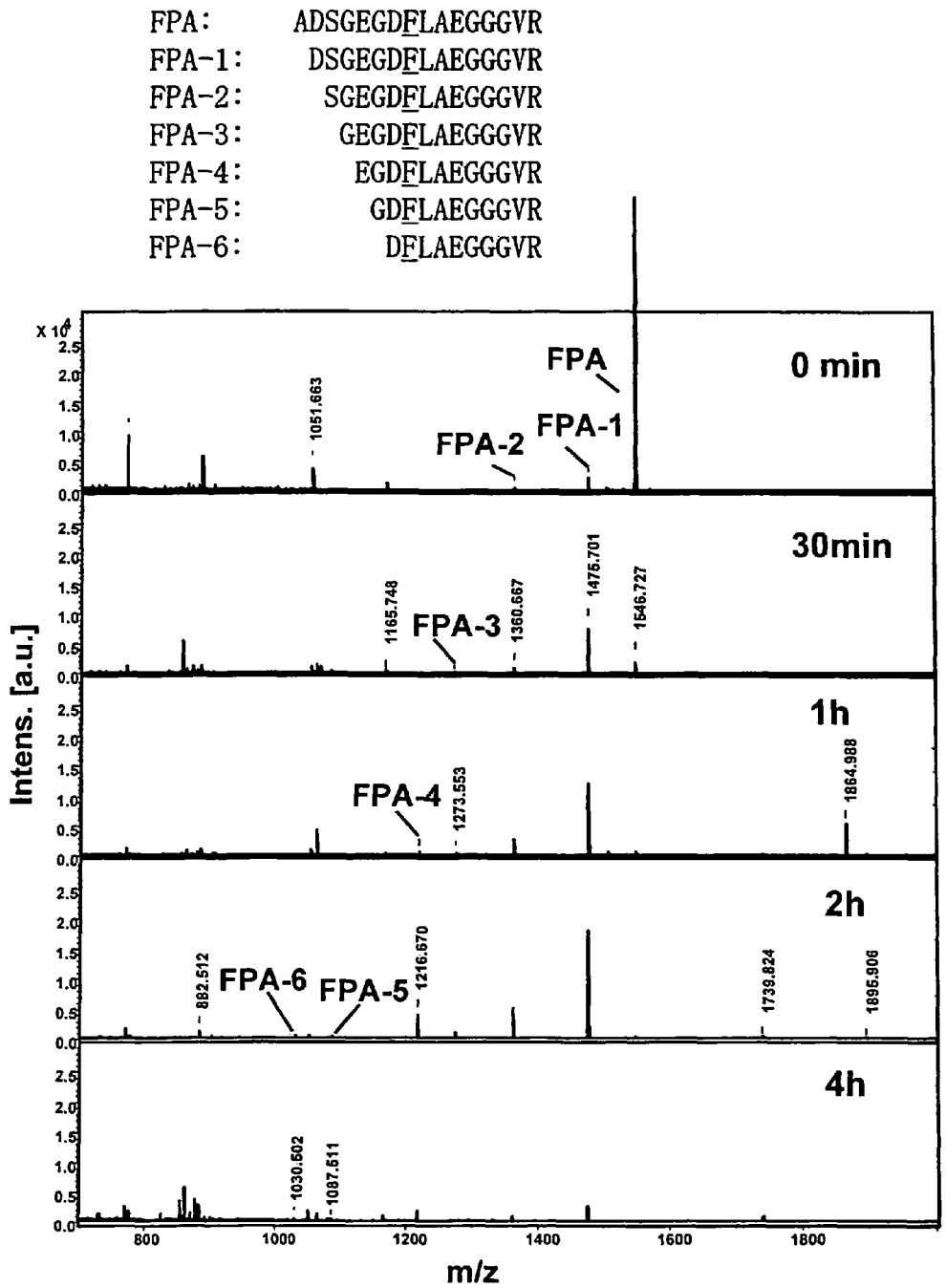
FIG. 3 illustrates the degradation products of FPA, and the intensities of such degradation products in a heparin plasma sample as a function of time (SEQ ID NOS 1-7, respectively, in order of appearance).

As the proteins degrade in a collected biological sample, such as blood, various degradation products are typically produced. For example, as shown in FIG. 3, FPA is degraded sequentially into smaller "daughter" peptides, with truncations of one amino acid residue at a time, from the amino terminal end, resulting in a family of degraded peptides each being one residue "shorter", designated FPA-1, FPA-2, FPA-3, FPA-4, FPA-5, and FPA-6. These degradation products are fragments of the original peptide. In the case of FPA, they are formed as proteases, a class of enzymes that cleave and degrade proteins or peptides, remove amino acids from FPA at its amino-terminus. The process is sequential and repetitive, and is described in the working example herein as a Sequential Multi-step Reaction (SMSR). The protease activity has an apparent dependence on the chemical identity of each "new" end that is exposed, such that each subsequent cleavage event happens at a unique rate, which may have little or no influence from the previous steps of the degradation process.

Each of the degradation products, as illustrated in FIG. 3 for example, may therefore express or exhibit a different half-life during all or a portion of their existence ex-vivo. In some cases, a protein, peptide, or degradation product thereof may exhibit a half-life while only in a valid time-frame. Therefore, an invalid time-frame may exist, which as used herein refers to a time period past collection where the half-life behavior is not expressed (e.g., when the degradation product is being produced). The half-life is an apparent half-life, and as used herein, refers to the rate at which the protein or peptide or degradation product thereof deteriorates, while still existing in a measurable quantity. The half-life is found by measuring protein, peptide, or degradation product expression, existence, or concentration as a function of time or time and environment, and determining a half-life model representation, typically using a mathematical model representative of the system. While a multi-variable mathematical model is demonstrated below to identify a half-life for all or a portion of the degradation products, other models may be appropriate given the nature of the protein, peptide, or degradation product system, as one skilled in the art may be able to determine.

The half-life of a protein or peptide expressed and/or measured will vary depending at least upon several ex-vivo factors, including chemical nature of the collected sample and the environment to which the sample is exposed during collection and/or subsequent processing and diagnostic measurements. For example, Table 1 provides some examples of half-lives for three potentially interesting diagnostic markers in various kinds of blood collection environments, including serum and alternatively anticoagulated plasmas. As mentioned above, these half-lives exhibit or express half-life behavior in all or a portion of their existence ex-vivo (i.e, valid and invalid timeframes).

TABLE 1

| $T_{1/2}$ (h) | Citrate | Serum | Heparin | EDTA |
|---|---|---|---|---|
| | | Half-lives of peptides | | |
| FPA | <0.1 | 0.30 ± 0.01 | 0.55 ± 0.02 | 3.51 ± 0.05 |
| C3f | 0.039 ± 0.01 | 0.079 ± 0.01 | 0.075 ± 0.01 | 0.082 ± 0.01 |
| C4 | 0.19 ± 0.01 | 0.59 ± 0.03 | 0.57 ± 0.02 | 2.63 ± 0.90 |

Figure 2:
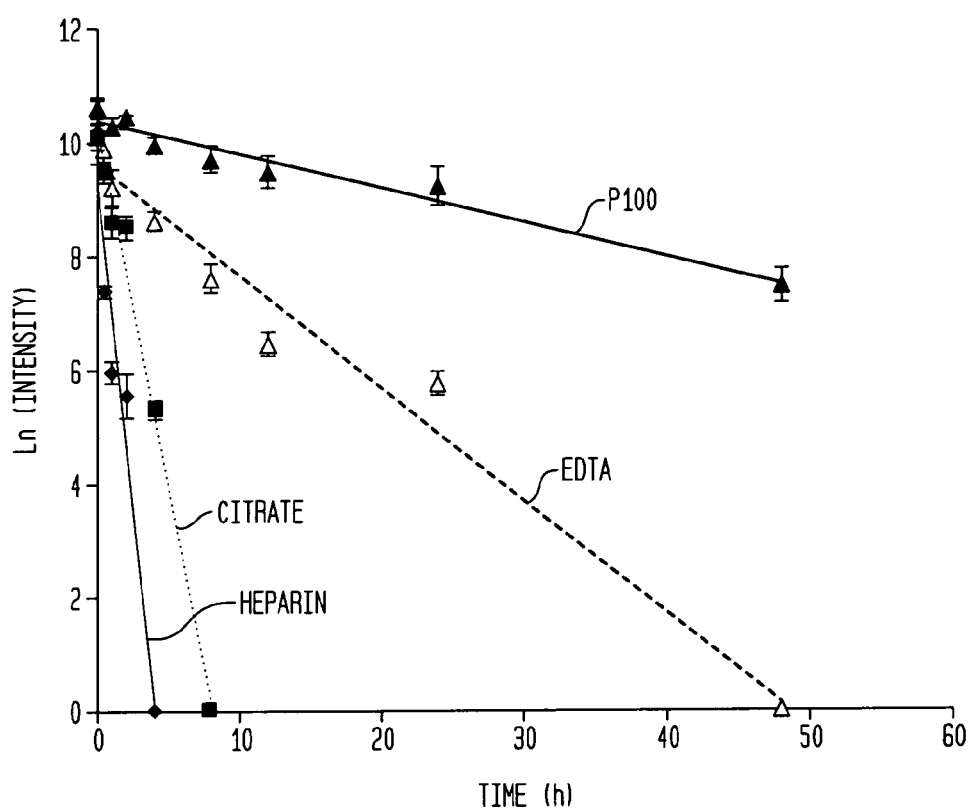
FIG. 2 is a graphical illustration of the degradation of peptides in various samples.

Methods of determining the half-lives of parent peptides may be determined by a process, which includes by example first spiking the peptide into one or more collection vehicles such as blood collection tubes comprising samples of biological fluid. In some embodiments, the collection vehicle is a swab. As described in an example disclosed herein, commercially available blood collection tubes sampled for determining half-lives included P100, EDTA, citrate, or heparin blood collection containers. The peak intensities of the peptide in each sample are measured at various points in time. For example, as shown in FIG. 1, peak intensity is measured at time 0, 0.5 hours, 1, 2, 4, 8, 12, 24, and 48 hours. The measured peak intensities in each sample may then be plotted graphically, as shown in FIG. 2, where the x-axis represents time and the y-axis represents the log of the peak intensity. A roughly linear relationship is observed between the log of peak intensity versus reaction time, suggesting that degradation occurs, to a first approximation, according to a first-order reaction (degradation). Accordingly, a line may be constructed for each sample. The slope of the line ($-k_{obs}$), representing the kinetic rate of the first-order degradation, may be used to compute a half-life value. That is, a kinetic rate constant can be determined by fitting the data with: $Ln(I)=-k_{obs}t+C$, where I is the peak intensity, or the peak area, t is the incubation time period in the study, C is a constant, and $k_{obs}$ is the observed (or apparent) rate constant. The half-life of the peptide is determined by $t_{1/2}=Ln(2)/k_{obs}$.

Determining half-lives of the degradation products of the peptide, however, entails further modeling and calculations. For examples, sequential multi-step reaction (SMSR) model may be used. Particularly, the half-life of each daughter peptide (e.g., FPA-1, FPA-2, FPA-3, etc.) is determined using information related to one or more of its parent peptides as well as the measured behavior of the daughter peptides creation and further degradation. Accordingly, as represented below, the peptide FPA, referred to as "a" and having a kinetic rate constant $k_1$, is used to determine the half-life of FPA, referred to as "b" and having a kinetic rate constant $k_2$, which is used to determine the half-life of FPA-2, referred to as "c" and having a kinetic rate constant of $k_3$, and so on.

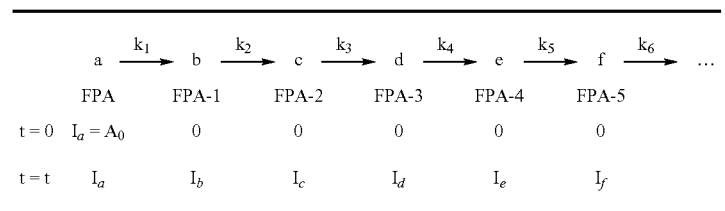

Accordingly, $k_j$ is the kinetic rate constant of step reaction j. $I_i$ is the measured signal (i.e., the peak intensity in MALDI-TOF MS) of peptide i. For example, measured intensities of each of the degradation products of the peptide over a 4 hour time span may be seen in FIG. 3. The peak intensity of, for example, FPA-4, occurs at 2 hours, where is measures 1216.670 m/z. $A_0$ is the initial peak intensity of the parent peptide at time 0. Since $I_i = K'_i C_i + I_0$, and $I_0 = 0$ after baseline subtraction, then $$I_i = K'_i C_i \text{ or } C_i = K_i I_i \quad (1),$$

where $$K_i = \frac{1}{K'_i},$$

which is a correlation constant between concentration and intensity of peptide i.

Kinetic rates are:

$$\frac{dC_a}{dt} = -k_1 C_a, \quad (2)$$

where, as discussed above, $k_1$ is the negative slope of the linear representation of degradation of the parent peptide.

$$\frac{dC_b}{dt} = k_1 C_a - k_2 C_b \quad (3)$$

$$\frac{dC_c}{dt} = k_2 C_b - k_3 C_c \quad (4)$$

$$\frac{dC_d}{dt} = k_3 C_c - k_4 C_d \quad (5)$$

$$\frac{dC_e}{dt} = k_4 C_d - k_5 C_f \quad (6)$$

To determine the value of $k_j$, equation (1) is inserted into equations from (2) to (6), thus, obtaining equations (2a)-(6a):

$$\frac{dI_a}{dt} = -k_1 I_a \quad (2a)$$

$$\frac{dI_b}{dt} = k_1 \frac{K_a}{K_b} I_a - k_2 I_b, \text{ or,}$$

$$\frac{dI_b}{dt} = k'_1 I_a - k_2 I_b \quad (3a)$$

where $k'_1 = k_1 \frac{K_a}{K_b}$.

Similarly, $$\frac{dI_c}{dt} = k'_2 I_b - k_3 I_c \quad (4a)$$

where $k'_2 = k_2 \frac{K_b}{K_c}$, $$\frac{dI_d}{dt} = k'_3 I_c - k_4 I_d \quad (5a)$$

where $k'_3 = k_3 \frac{K_c}{K_d}$, $$\frac{dI_e}{dt} = k'_4 I_d - k_5 I_e \quad (6a)$$

where $k'_4 = k_4 \frac{K_d}{K_e}$.

Equations (2a) through (6a) may then be sequentially integrated, thereby producing equations (2b)-(6b):

$$I_a = A_0 e^{-k_1 t} \quad (2b)$$

$$I_b = \frac{A_0 k'_1}{k_2 - k'_1} \left[ e^{-k'_1 t} - e^{-k_2 t} \right] \quad (3b)$$

$$I_C = \frac{A_0 k'_1 k'_2}{(k_2 - k'_1)(k_3 - k'_1)(k_3 - k_2)} \left[ (k_3 - k_2) e^{-k'_1 t} - (k_3 - k'_1) e^{-k_2 t} + (k_2 - k'_1) e^{-k_3 t} \right] \quad (4b)$$

The derivation of equation (4b) is listed briefly as below:

Combining equations (3b) and (4a) to obtain:

$$\frac{dI_C}{dt} = \frac{A_0 k'_1 k'_2}{k_2 - k'_1} \left[ e^{-k'_1 t} - e^{-k_2 t} \right] - k_3 I_C$$

$$I_C = e^{-k_3 t} \int^\tau e^{(k_3 t)} \frac{A_0 k'_1 k'_2}{k_2 - k'_1} \left[ e^{-k'_1 t} - e^{-k_2 t} \right] dt + C e^{-k_3 t}$$

$$I_C = e^{-k_3 t} \frac{A_0 k'_1 k'_2}{k_2 - k'_1} \left[ \frac{1}{k_3 - k'_1} e^{(k_3 - k'_1)t} - \frac{1}{k_3 - k_2} e^{(k_3 - k_2)t} \right] + C e^{-k_3 t}$$

Applying initial condition, at $t=0$, $I_c=0$, to the above equation to solve C, we obtained $I_c$ as in equation (4b). Similarly, $I_d$ and $I_e$ can be obtained.

$$I_d = \frac{A_0 k_1' k_2' k_3'}{(k_4 - k_1')(k_4 - k_2)(k_4 - k_3)} \left[ e^{-k_1't} - e^{-k_2t} + e^{-k_3t} - e^{-k_4t} \right] \quad (5b)$$

$$I_e = \frac{A_0 k_1' k_2' k_3' k_4'}{(k_4 - k_1')(k_4 - k_2)(k_4 - k_3)} \left\{ \begin{array}{l} \left[ \frac{1}{k_5 - k_1'} e^{-k_1't} - \frac{1}{k_5 - k_2} e^{-k_2t} + \frac{1}{k_5 - k_3} e^{-k_3t} - \frac{1}{k_5 - k_4} e^{-k_4t} \right] - \\ \left[ \frac{1}{k_5 - k_1'} - \frac{1}{k_5 - k_2} + \frac{1}{k_5 - k_3} - \frac{1}{k_5 - k_4} \right] e^{-k_5t} \end{array} \right\} \quad (6b)$$

Figure 4B:
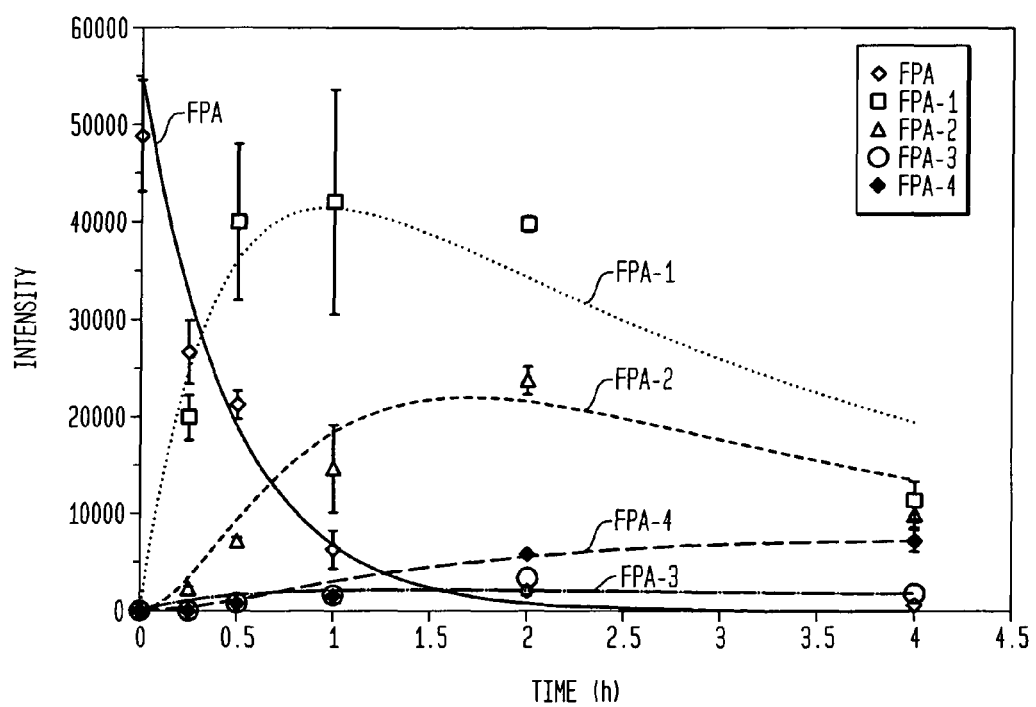
FIG. 4B is a graphical representation of the sequential degradation of FPA peptides.

Such calculations are performed for different points in time (i.e., different values of t), so as to plot the varying intensities of each degradation product against the reaction time, as shown in FIG. 4b. The rate constant of each step reaction, $k_j$, can be computed by simulation of the equations (2b)-(6b). Then, the half-lives for each degradation product may be calculated by the equation $t_{1/2} = Ln(2)/k_j$.

Due to the complexity of the equations, calculation of half-lives of the degradation products may most efficiently be performed by a computational device, such as the device 120 described below with respect to FIG. 5. Furthermore, the half-life value expressed by a given parent or daughter protein or peptide may not exist at all moments of time, but rather a subset of time wherein the behavior is representable as a half-life. Implementation of such a device may prove most beneficial with regard to performing simulation of the degradation of each daughter peptide by creating the curves shown in FIG. 4b.

The measurement of half-life simply depends on having a robust measurement system in place, and monitoring the levels of any one analyte as a function of time. A measurement system could include, but not limited by, Mass Spectrometry (MS) based instruments (GC-MS, ESI-MS, MALDI-TOF MS and so on), immunological assay methods (ELISA, RIA), spectrometry based method (UV/VIS), and electrophoresis based methods. In some embodiments, measurement is performed using matrix-assisted laser desorption ionization time-of-flight mass spectrometry (MALDI-TOF MS), which is a method of measuring molecules based directly on their mass and concentration. It is well known to those skilled in the arts. A thorough description of the technique itself can be found, for example, in Yi et al., J. Proteome Res. 6(5):1768-81 (2007).

In some instances, the half-life of one or more of the degradation products may be greater than that of the original, full-size or parent protein or peptide itself. For example, as seen in Table 2, the half-life of degradation product FPA-1 is actually longer than that of its parent peptide, FPA. Moreover, it is also larger than that of its own daughter peptide, FPA-2. Further, the half-life of FPA-4 is significantly longer than any of its parent peptides.

TABLE 2

Half-lives of degradation products in heparin.

| Protein/Product | $T_{1/2}$ (h) in Heparin |
|---|---|
| FPA | 0.29 |
| FPA-1 | 2.1 |
| FPA-2 | 0.31 |
| FPA-3 | 0.38 |
| FPA-4 | 15.2 |

Due to the longer half-lives of some degradation products as compared to the original protein or peptide and the other degradation products thereof, it is advantageous to determine whether the known or suspected marker itself, i.e., the full length peptide, or one of its degradation products should be measured. A determination of which degradation product to measure may, at least in part, be based on the relevant timeframe during which such measurement or analysis will be performed. Such a timeframe can account for the setting of the test (e.g. a remote doctor's office versus a hospital inpatient), the environment to which the sample is exposed between acquisition and analysis, and the nature of the sample and analyte. Thus, according to one aspect of the invention, diagnosis of diseases may be performed by measuring presence or amount of a targeted protein or a degradation product of the protein in a collected biological sample as a marker for the disease condition, wherein the targeted protein or degradation product is selected for measurement based on a prior identification of a measurable half-life at a predetermined time period between collection and measurement. The measurement of the targeted protein or degradation product may then be correlated with the presence or absence of the disease condition.

Some or all of the steps involved in identifying the protein or degradation product to be measured may be performed by a computing device 120. The computing device 120 may comprise any device capable of processing instructions and transmitting data to and from humans, such as a personal computer, personal digital assistant (PDA), cellular phone, etc. As shown in FIG. 5, the computing device 120 contains a processor 122, memory 124 and other components typically present in general purpose computers.

Memory 124 stores information accessible by processor 122, including instructions 130 for execution by the processor 122 and data 135 which is retrieved, manipulated or stored by the processor. The memory 124 may be of any type capable of storing information accessible by the processor 122, such as a hard-drive, ROM, RAM, CD-ROM, USB jump drive, write-capable, read-only, or the like.

The instructions 130 may comprise any set of instructions to be executed directly (such as machine code) or indirectly (such as scripts) by the processor. In that regard, the terms "instructions," "steps" and "programs" may be used interchangeably herein. The functions, methods and routines of the program in accordance with the present invention are explained in more detail below.

Data 135 may be retrieved, stored or modified by processor 122 in accordance with the instructions 130. The data 135 may be stored as a collection of data. For instance, although the invention is not limited by any particular data structure, the data may be stored in computer registers, in a relational database as a table having a plurality of different fields and records, as an XML. The data may also be formatted in any computer readable format such as, but not limited to, binary values, ASCII or EBCDIC (Extended Binary-Coded Decimal Interchange Code). Moreover, any information sufficient to identify the relevant data may be stored, such as descriptive text, proprietary codes, pointers, or information which is used by a function to calculate the relevant data.

Figure 5:
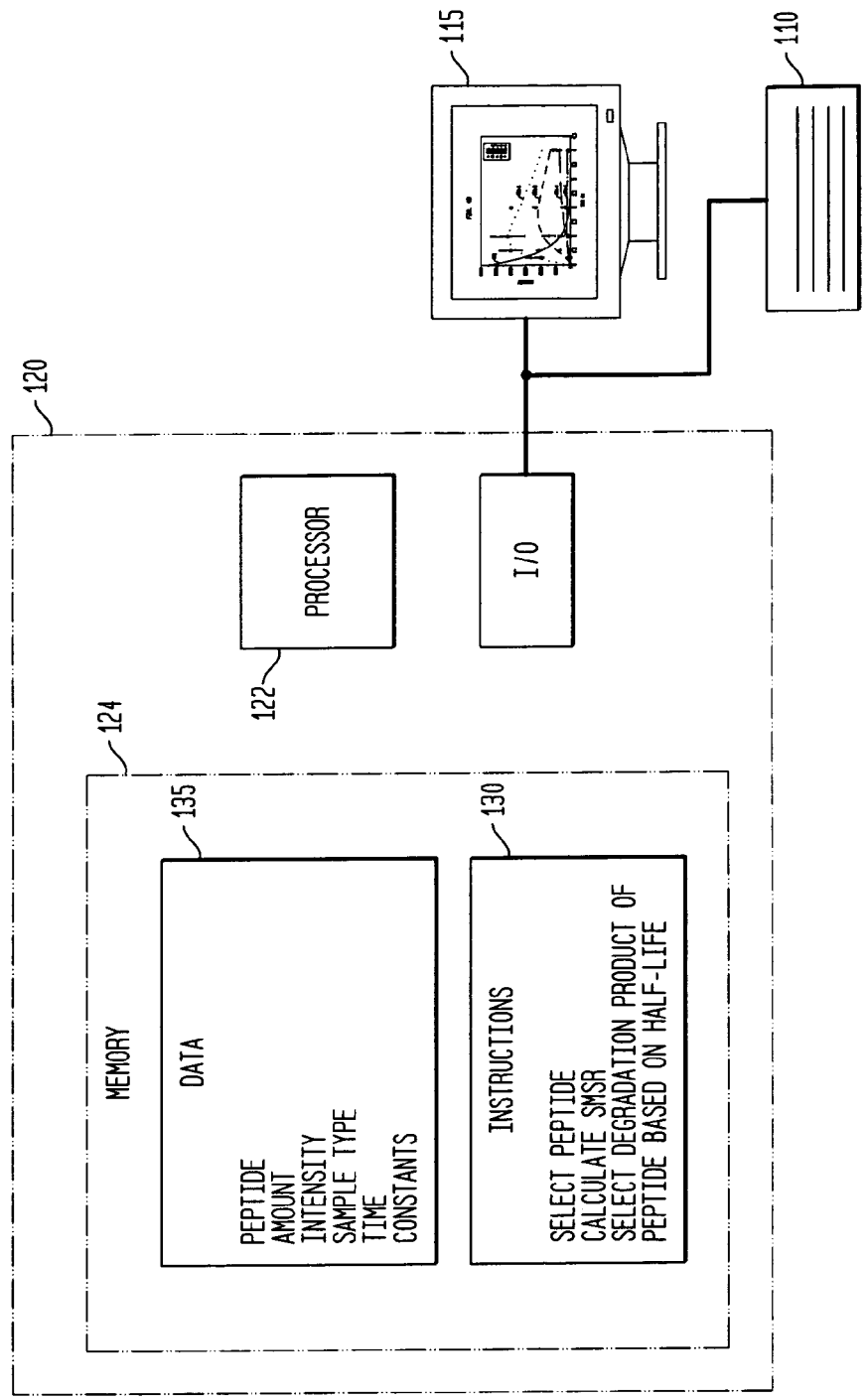
FIG. 5 is a representation of a system according to an aspect of the invention.

Although the processor 122 and memory 124 are functionally illustrated in FIG. 5 within the same block, it will be understood by those of ordinary skill in the art that the processor and memory may actually comprise multiple processors and memories that may or may not be stored within the same physical housing. For example, some or all of the instructions and data may be stored on removable CD-ROM and others within a read-only computer chip. Some or all of the instructions and data may be stored in a location physically remote from, yet still accessible by, the processor. Similarly, the processor may actually comprise a collection of processors which may or may not operate in parallel.

The computing device 120 may comprise additional components typically found in a computer system such as a display 115 (e.g., an LCD screen), user input 110 (e.g., a keyboard, mouse, game pad, touch-sensitive screen), modem (e.g., telephone or cable modem), and all of the components used for connecting these elements to one another.

The computing device 120 may be used to identify a peptide or degradation product thereof to be measured in determining the presence or absence of a disease condition. For example, a user may select a protein or peptide known as, or thought to be, a marker for a particular disease. For example, FPA may be selected as a known marker for ovarian cancer. Alternatively, a user may input a particular disease condition, and the processor 122 may appropriately match that condition to one of a preprogrammed list of peptide or proteins. Based on the selection, the processor 122 may determine the degradation products of the peptide, and the half-lives of each degradation product. The processor may perform such analysis using SMSR (a sequential multi-step reaction) model.

The results of such analysis may be output to the user via the display 115. Such results may be conveyed in any number of ways, such as graphically, textually, etc. For example, the results may be portrayed in the form of a graphical simulation of the sequential degradation of the peptides, as shown in FIG. 4. Alternatively, the results may be portrayed in the form of a table listing the degradation products with their corresponding half-lives, such as in Table 2.

Based on the output, a peptide or degradation product may be selected for testing. For example, such selection may be performed by the user, by determining which degradation product(s) will exist in a measurable amount at a predetermined period of time. This predetermined period of time may be any time in the future, but should include the time between collection of a sample and testing of the sample. Alternatively or additionally, the computing device 120 may provide one or more recommendations for selections by the user. For example, with reference to the example discussed above, the computing device 120 may suggest that FPA-1 be selected for biomarker testing if the testing will be performed 4 hours after collection of the sample, or that FPA-4 be selected if the testing is to be performed 48 hours after collection of the sample.

Because the half-lives may vary depending on a substance in which the sample interacts, the processor may perform such analysis with respect to one or more different types of substances. For example, degradation of the sample may be analyzed in collection vehicles containing heparin, citrate, EDTA, or any other additives to which the sample is exposed during or after collection. Additionally, the computing device 120 may also suggest a type of plasma sample to be used for collection of the sample, based on comparison of measurements between alternative sample types, if such data can be accumulated and provided for analysis.

According to another aspect, a laboratory information system (herein LIS system) may be interfaced with the computing device. The LIS system may incorporate information relating to an anticipated amount of time that would elapse from collection of a sample to analysis of the sample, and suggest a collection vehicle and respective handling conditions for the sample to be transported to an instrument analyzer for diagnostic measuring or assaying to occur. The computing device may then use an actual or expected time for when the collection of the sample occurred to influence when the sample is to be assayed. The computing device may determine if the time from collection to measurement, possibly along with inclusion of the specific collection vehicle, as to whether or not the elapsed time is a valid or invalid timeframe for when a daughter peptide can be measured.

According to another aspect, the input to the computing device 120 may include the predetermined time period between collection of the sample from the patient and analysis of the sample, a proposed type of substance with which the sample may interact, and handling conditions of the sample during the predetermined time period. The processor 122 may take such variables into account in simulating degradation of the peptide, and in recommending a peptide or degradation product for testing to diagnose a disease condition.

For example, the user may input that testing will be performed 48 hours after collection of the sample. The computing device 120 may perform the simulation, and output the results to the user. The output may be simplified to highlight the intensities of the peptide and each of its degradation products at the predetermined time period. Moreover, the computing device may indicate whether any of the peptide or degradation products will exist in measurable quantities during such time period.

Biological samples that may be collected and used in the presently disclosed methods typically include any body fluid withdrawn from a patient. Representative examples of such samples thus include whole blood (and derivatives or components thereof including plasma, serum, red blood cell concentrates, platelet concentrates, and leukocyte concentrates), tissue, bone marrow aspirates, cerebral spinal fluid, feces, urine, cultured cells, saliva, oral secretions, nasal secretions, bronchial lavage, and the like.

Biological samples may be collected, processed and stored in accordance with standard collection vehicles and procedures known in the art. The sample collection system of the present invention can encompass any collection vehicle including, but not limited to, tubes such as test tubes and centrifuge tubes; closed system blood collection vehicles, such as collection bags or evacuated tubes; syringes, especially pre-filled syringes; catheters; microtiter and other multi-well plates; arrays; tubing; laboratory vessels such as flasks, spinner flasks, roller bottles, vials, microscope slides, microscope slide assemblies, coverslips, films and porous substrates and assemblies; pipettes and pipette tips, etc.; tissue and other biological sample collection containers; and any other container suitable for holding a biological sample, as well as containers and elements involved in transferring samples. In some embodiments, the collection vehicle is a tube tube having a separating member (e.g., a mechanical separating element or a gel) for separating blood components is used. In such aspect, the interior of the tube and/or the exterior of the separating member may be treated with a stabilizing agent.

Plastic or glass is often used to manufacture the collection vehicle used in the present invention. Some preferred materials used to manufacture the collection device include polypropylene, polyethylene, polyethyleneterephthalate, polystyrene, polycarbonate and cellulosics. More expensive plastics such as polytetrafluoroethylene and other fluorinated polymers may also be used. In addition to the materials mentioned above, examples of other suitable materials for the collection devices used in the present invention include polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF and perfluoroalkoxy resins. Glass products including silica glass are also used to manufacture the collection devices. One exemplary glass product is PYREX®) (available from Corning Glass, Corning, N.Y.). Ceramic collection devices can be used according to embodiments of the invention. Cellulosic products such as paper and reinforced paper containers can also be used to form collection vehicles according to the invention.

In some embodiments, the collection vehicle contains a stabilization agent such as an agent that affects clot formation. Such agents may accelerate or inhibit clot formation. Blood collected in evacuated tubes often must be clotted prior to clinical examination. It is desirable to form a dense clot as rapidly and completely as possible to facilitate clean separation of the clot and the cells trapped within the clot from the serum layer by centrifugation. To achieve this end, both plastic and glass blood collection tubes frequently employ a clot activator. Typical activators are diatomaceous earth and particles of inorganic silicates, or biochemicals such as ellagic acid, thrombin and thromboplastin. In one line of commercial blood collection tubes, for example, a coating of silicate particles in polyvinylpyrrolidone (PVP), a water soluble polymer) is affixed to the inside of the tube. When blood enters the tube, the PVP dissolves and silicate particles are released to initiate clotting. The PVP enters both the serum and clot.

In other embodiments, and as described above, the collection vehicle contains a stabilization agent that inhibits blood coagulation. Typically, the anti-coagulation additive is ethylenediaminetetra-acetic acid (EDTA), in various alternative salt forms including sodium, potassium or lithium, in liquid or dried forms; heparin, in various salt forms, at various polymer size ranges, and in liquid or dried forms; or buffered citrate, typically in an aqueous solution. Blood collection tubes containing an anticoagulant are commercially manufactured and sold. An example of such a tube is disclosed in U.S. Pat. No. 5,667,963 to Smith, et al. The inclusion of such an agent may be desirable to prevent the aggregation due to platelet activation.

In some embodiments, the stabilizing agent includes a mixture of anti-coagulants including two or more of: (a) theophylline, (b) adenosine and/or 2-chloroadenosine, (c) dipyridamole, and (d) citrate. See, e.g., U.S. Pat. No. 7,011,938.

Thus, in some embodiments, the collection vehicles include a serum tube, a serum tube with density separator, a citrate tube, a heparin tube, an EDTA tube, an EGTA tube, a CTAD tube, and a sodium fluoride tube.

Degradation of peptides may also be inhibited by addition of EDTA and/or proteolysis inhibitors, also known as protease inhibitors, to the collection vehicle and/or the sample once it is collected into the vehicle. For example, U.S. Pat. No. 5,541,116 discloses the use of two protease inhibitors, anastatin and leupeptin, in combination with EDTA for stabilizing peptides in whole blood, serum or plasma samples. The patent, however, discloses stabilizing the samples by adding an adequate amount of the stabilizing combination to the samples themselves after they have been obtained or after thawing in situations where the sample had previously been frozen after collection thereof. U.S. Pat. No. 7,309,468 teaches blood collection vehicles that contain mixtures of protease inhibitors.

Handling conditions of the collected sample may in some circumstances affect the half-lives of the peptides and degradations products in the collected sample. For example, the sample may be kept at room temperature, or exposed to ambient conditions such as during shipping in a delivery truck or airplane, or may be subjected to freezing or cryopreservation conditions. Moreover, the sample may be transferred from the collection vehicle to a second or third vehicle. Accordingly, such handling conditions may be considered in the analysis of degradation of the peptides.

Regardless of the collection environment used for analysis, the collection vehicle, handling environment, and handling conditions must be taken into account as part of the diagnostic measurement. Any conditions, including sample collection and handling variables, can be tested beforehand as part of the model training process, and an appropriate analyte form can be selected for analysis in subsequent diagnostic applications.

Representative examples of peptide biomarkers and degradation products (in addition to fibrinogen α) that may be identified and measured in accordance with the methods of the present invention are set forth in Table III.

TABLE III

| PEPTIDE | DEGRADATION PRODUCTS | SEQ ID NO:<br>PEPTIDE<br>WITHOUT<br>(AMI-<br>NO ACID) | SEQ ID NO: |
|---------|---------------------|-------------------------------------------------------|------------|
| FPA | (full length peptide) ADSGEGDFLAEGGGVR | | 1 |
|  | DSGEGDFLAEGGGVR | | 2 |
|  | SGEGDFLAEGGGVR | | 3 |
|  | GEGDFLAEGGGVR | | 4 |
|  | EGDFLAEGGGVR | | 5 |
|  | GDFLAEGGGVR | | 6 |
|  | DFLAEGGGVR | | 7 |
|  | FLAEGGGVR | | 8 |
|  | LAEGGGVR | | 9 |
| Fibrinogen α | (K) SSSYSKQFTSSTSYNRGDSTFESKSYKMA<br>(full length peptide) | 10 | 11 |
|  | (K) SSSYSKQFTSSTSYNRGDSTFESKSYKM | 12 | 13 |
|  | (K) SSSYSKQFTSSTSYNRGDSTFESKSY | 14 | 15 |
|  | (K) SSSYSKQFTSSTSYNRGDSTFESKS | 16 | 17 |

TABLE III-continued

| PEPTIDE | DEGRADATION PRODUCTS | SEQ ID NO: PEPTIDE WITHOUT (AMINO ACID) | SEQ ID NO: |
|---|---|---|---|
|  | (K) SSSYSKQFTSSTSYNRGDSTFES | 18 | 19 |
|  | SSYSKQFTSSTSYNRGDSTFE |  | 20 |
| C3f | (full length peptide) SSKITHRIHWESASLLR |  | 21 |
|  | SSKITHRIHWESASLL. |  | 22 |
|  | SKITHRIHWESASLL. |  | 23 |
|  | KITHRIHWESASLL. |  | 24 |
|  | ITHRIHWESASLL. |  | 25 |
|  | THRIHWESASLL. |  | 26 |
|  | HRIHWESASLL. |  | 27 |
|  | RIHWESASLL. |  | 28 |
|  | IHWESASLL. |  | 29 |
|  | HWESASLL. |  | 30 |
|  | SSKITHRIHWESASL.. |  | 31 |
| C4a | (full length peptide) RNGFKSHALQLNNRQI (R) | 32 | 33 |
|  | NGFKSHALQLNNRQI (R) | 34 | 35 |
|  | NGFKSHALQLNNRQ. |  | 36 |
|  | NGFKSHALQLNNR.. |  | 37 |
|  | (R) GLEEELQFSLGSKINVKVGGNSKGTLKVLR (full length peptide) | 38 | 39 |
|  | (R) GLEEELQFSLGSKINVKVGGNSKGTL | 40 | 41 |
|  | (R) GLEEELQFSLGSKINVKVGGNS | 42 | 43 |
|  | (R) GLEEELQFSLGSKINVR | 44 | 45 |
| ITIH4 | (R) QAGAAGSRMNFRPGVLSSRQLGLPGPPD-VPDHAAYHPF (full length peptide) | 46 | 47 |
|  | MNFRPGVLSSRQLGLPGPPDVPDHAAYHPF. |  | 48 |
|  | PGVLSSRQLGLPGPPDVPDHAAYHPF. |  | 49 |
|  | GVLSSRQLGLPGPPDVPDHAAYHPF. |  | 50 |
|  | SSRQLGLPGPPDVPDHAAYHPF. |  | 51 |
|  | SRQLGLPGPPDVPDHAAYHPF. |  | 52 |
|  | QLGLPGPPDVPDHAAYHPF. |  | 53 |
|  | GLPGPPDVPDHAAYHPF. |  | 54 |
|  | HAAYHPF. |  | 55 |

Yet other examples of biomarkers and conditions for which the present invention may be useful include, but are certainly not limited to brain natriuretic peptide as a marker of myocarditis in patients with Kawasaki disease (Kawamura, et al., Cardiology in the Young 12:153-58 (2002); S-100β protein for cerebral oedema complicating severe diabetic ketoacidosis (McIntyre, et al., Diab. Med. 17(11):807-9 (2000); plasma and serum biomarkers of cognitive decline and Alzheimer's (Solfrizzi, et al., Clinica chimica acta 364(1-2): 91-112 (2006); plasma endothelin-1 precursor for obstructive sleep apnea (Jordan, et al., Peptides 26(9):1654-60 (2005) plasma B-Type Natriuretic peptide for patients with pleural effusions (Gegenhuber, et al., Chest 128:1003-09 (2005); osteoclin, a calcium-binding bone protein, for bone turnover (Polak-Jonkisz, et al., Nepthrology 4(5-6):339-46 (2007) surfactant aproprotein, procollagen III and TGF-β for predictors of pulmonary effects of radiation (McDonald, et al., Rad. Oncol. Invest. 3(2):56-63 (2006); and alveolar type-I cell-specific protein $RTI_{40}$, for lung injury (Newman, et al., Am. J. Respir. Crit. Care Med. 161(3):990-5 (2000).

Working Example

A direct test for stability of a peptide biomarker in a collected blood sample was carried out by monitoring its change during a time-course incubation. It was discovered that the spiked peptides themselves are subject to preanalytical degradation, and thus the spiked peptides became our focus for studying the relative instability of peptides in various blood samples. The stability of AQUA FPA was tested by adding it into either a serum or plasma sample (either BD P100, EDTA, citrate, or heparin plasma) collected from a single venipuncture, or a pooled serum or plasma sample from three healthy individuals. After the spiked sample was incubated for specified periods of time, the peptides were measured by MALDI-TOF MS.

Human blood from healthy individuals was directly drawn into evacuated tubes to obtain serum and plasma samples, as described previously (20). Briefly, serum tubes (BD product #366430) were placed at room temperature (r.t., approx. 24° C.) to clot for 60 min after the collection of the blood, and then centrifuged at 2,500×g for 15 min. at room temperature. Plasma tubes, including citrate tube (BD product #369714), heparin tube (BD product #367886), EDTA tube (BD product #367525), and BD P100 tube (BD product #366456), were spun immediately (within 10 min. after blood was drawn), for 15 min at 2,500×g, and at room temperature to minimize the handling condition and to prevent possible platelet activation. Both plasma and serum samples were pipetted out of the blood-collection tubes into Eppendorf tubes and were frozen within 15 minutes at −80° C. until use. With these optimized handling processes, full acquisition and processing time was minimized to approximately 30 minutes for plasma and 90 minutes for serum.

Figure 6:
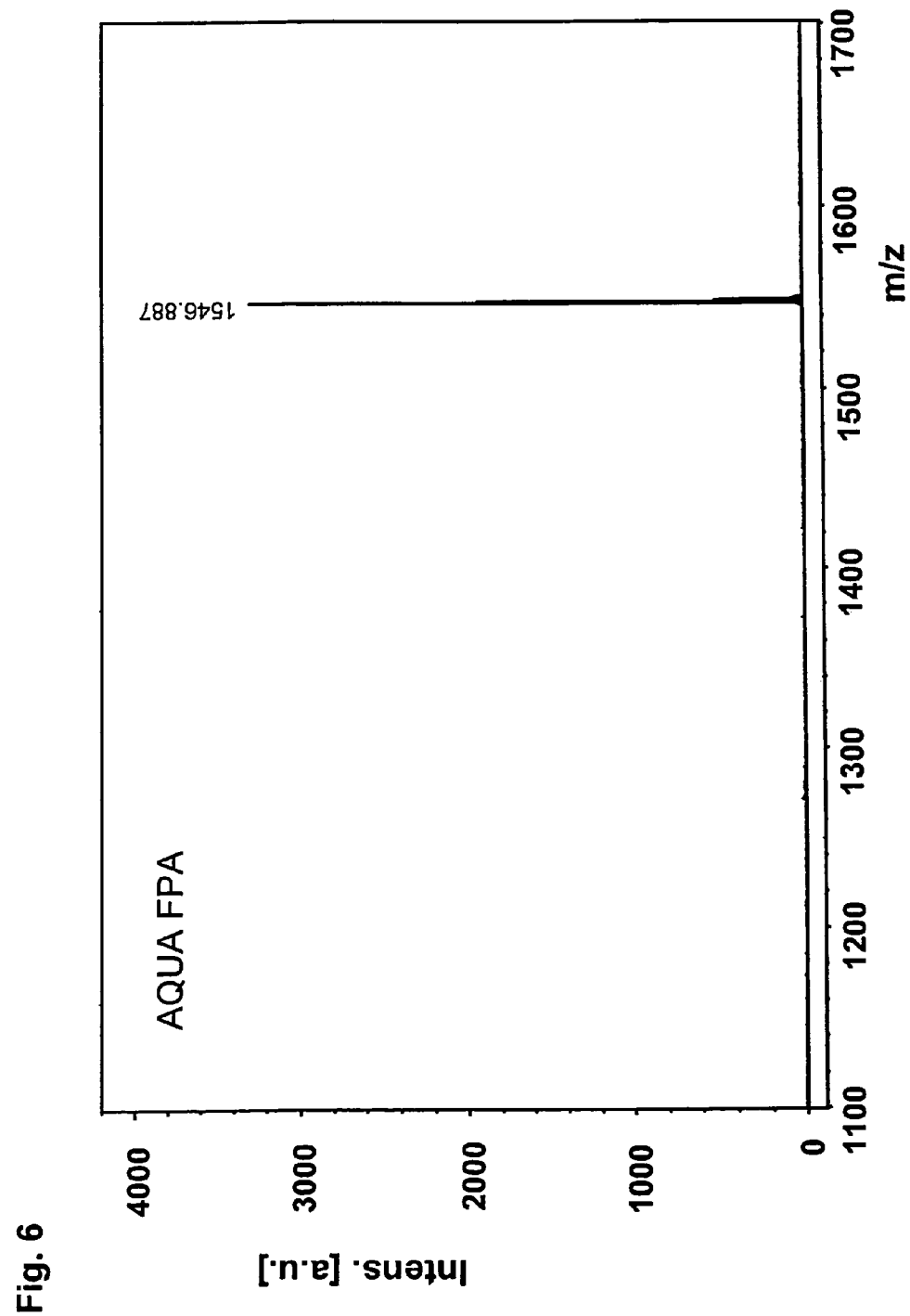
FIG. 6 is a printout from a mass spectra analysis of synthesized ACQUA FPA.

Isotopically labeled peptides were purchased from Sigma-Genosys (The Woodlands, Tex.). All peptides were synthesized with one stable isotopic amino acid residue, either L-Arginine-13C6 15N4, or L-Phenylalanine-13C9 15N1, with mass of 10 higher than its natural counterpart. The quality of each peptide was verified by HPLC, MALDI-TOF MS (FIG. 6), and amino acid analysis by the vendor with purity higher than 98%. Easily aqueous soluble peptides, including C4 (NGFKSHALQLNNRQIR (SEQ ID NO: 35)) and FPA (ADSGEGDFLAEGGGVR (SEQ ID NO: 1)) (the stable isotopic labeled residue are underlined, same hereinafter), are dissolved and diluted in water with 0.1% TFA. Peptides of lower solubility, such as C3f (SSKITHRIHWESASLLR (SEQ ID NO: 21)), were dissolved in 50% ACN solution. The peptides were diluted with relevant solvents to make stocks of 400 fmol/μL for spiking experiments.

The frozen serum and plasma were thawed (once only) in a room temperature water bath for approximately 5 minutes, in order to minimize the dwell time by temperature exposure of the samples. Soluble AQUA peptide (50 μL in water) was spiked into a thawed serum or plasma sample (450 μL), resulting in a final concentration of 40 fmol/μL. The samples were incubated at room temperature. A 45-μL aliquot was withdrawn at each specified time, and quenched by adding 5 μL of 2% TFA solution. The quenched sample was subsequently transferred onto a Microcon YM-3 (Millipore) and spun in a Micro Centrifuge (Eppendorf Centrifuge 5417R) at 12,500 r.p.m. and 10° C. for 45 minutes. The filtrate was collected, and desalted using Zip-Tip C18 (Millipore). The eluted peptides (1 μL) were mixed in 1:1 (v/v) ratio with 5 mg/mL of α-cyano-4-hydroxycynnamic acid (CHCA) as the matrix. The peptide mixture was spotted on a plate, air-dried, and analyzed using MALDI-TOF MS.

For the less soluble peptides, 1 μL peptide stock was added into 9 μL serum or plasma. After incubation for specified time period (0-72 hours), the sample was quenched with addition of 40 μL of ACN with TFA solution to a final 10% ACN and 0.2% TFA. The quenched samples were supplied for extraction using Zip-Tip C18 (Millipore), followed by MALDI-TOF MS analysis.

MALDI-TOF MS analysis was performed on an Ultraflex II MALDI-TOF MS (Bruker-Daltonics) as described previously (20). The final spectrum was calibrated externally, which allows a mass accuracy of better than 10 ppm. For quantitative analysis of AQUA peptides, the spectrum of each sample was obtained from accumulation of 30 qualified spectra, each of which was obtained from 100 laser shots under fixed laser power. The sample site targeted by the laser was moved automatically after each of 100 shots to prevent the sample from being over-burned. During the accumulation, the quality of each spectrum from the 100 shots was evaluated in terms of peak resolution and signal-to-noise ratio. A spectrum with less than 1000 peak resolution was filtered out. Under these settings, the CV % of a peptide peak intensity was 6-25% (average 15%) with this high resolution instrument (20), was better than average 18% CV reported previously with a Bench-Top instrument (31).

The MALDI-TOF mass spectra were processed by flex-Analysis (Bruker-Daltonics) with median smoothing and baseline subtraction. The peaks were detected with SNP algorithm and S/N threshold 3. The other parameters were the same as those in the default method. For comparative analysis, all of the time-course spectra were processed using the same parameters and the spectra were plotted in the same scale on x- and y-axes.

The stability of a peptide was analyzed by time-course MS-based kinetics analysis. The peak list including peak intensity was exported into Microsoft Excel using flexAnalysis (Bruker-Datonics). A roughly linear relationship was observed between the log of peak intensity versus reaction time, suggesting that degradation occurs, to a first approximation, according to a first-order reaction. The kinetic rate constant can be determined by fitting the data with: $Ln(I) = -k_{obs}t + C$, where I is the peak intensity, or the peak area, t is the incubation time period in this study, C is a constant, and $k_{obs}$ is the observed (or apparent) rate constant. Further, the half-life of the peptide is determined by $t_{1/2} = Ln(2)/k_{obs}$.

For determining kinetic rate constants in a complex sequential reaction observed in this study, analytical solutions were derived from, a first order sequential multi-step reaction (SMSR), as explained above in the discussion concerning equations (1)-(6), (2a)-(6a), and (2b)-(6b). MATLAB (Version 7.0, Mathworks) was employed to numerically simulate this model with the experimental data, and reaction rate constants were then determined in the sequential pattern following the chain reaction sequences. The modeling process was optimized to achieve a best fit to $R^2$ (goodness-of-fit) calculation.

Figure 7:
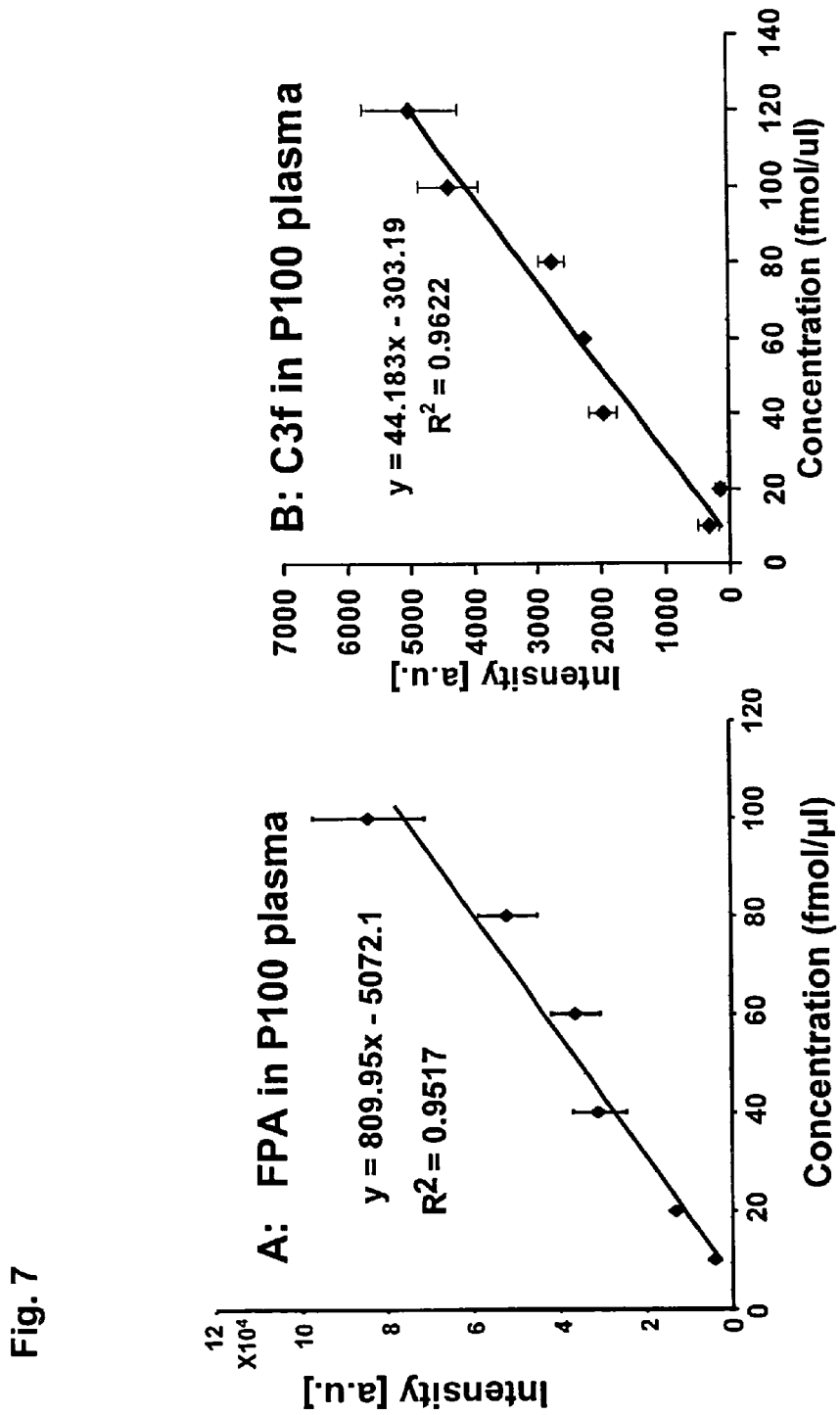
FIG. 7 is a graphical representation of a relationship between different attributes of particular peptides.

The change in labeled FPA (1546.69 m/z) abundance during time-dependent incubation, according to sample types (P100, EDTA, citrate, and heparin plasma samples), are shown with peak intensities normalized to ion count in FIG. 1. A decrease in peak intensity of the AQUA FPA is observed in all of these plasma samples, eventually achieving undetectable levels after some period of incubation. The peptide could not be detected above noise after four hours in heparin, eight hours in citrate, or 24 hours in EDTA. By contrast, the same peak was still easily detected at 48 hours in P100, suggesting that the protease inhibitors in P100 enhanced the stability of the spiked AQUA peptide. To demonstrate the quantitative nature of this analysis for monitoring protease catalyzed reactions, the dynamic range of these isotope-labeled peptide measurements was examined. A reasonably linear plot ($R^2 = 0.95$) of peak intensity versus the concentration of AQUA FPA that was spiked into the same P100 plasma samples in four replicates was observed with its concentration up to 100 fmol/μL (FIG. 7). A similar linearity was also observed on tested C3f peptide (FIG. 7), bradykinin and GLP-1 (data not shown). This analysis supports the use of the present method for semiquantitative measurement across approximately one order of magnitude in a complex sample such as plasma (32).

As shown on FIG. 2, the peak intensity (in nature logarithmic scale) of the parent labeled FPA peptide spiked into four plasma samples deceases in a linear manner as a function of reaction time at room temperature. The linearity of these plots indicates that AQUA peptide degradation follows a first-order reaction of kinetics, regardless of the sample types and peptides (Table 1) tested in this study, and thus the slopes of the plots reflect the apparent rate constants (k) of the degradation reactions. These rate constants and the corresponding half-lives of the spiked peptides are determined and listed in Table 1.

The half-life of the FPA peptide in serum was too short (less than 15 min., Table 1) to be measured in this format. Yet, the presence of protease inhibitors in P100 provided the highest level stability to the peptides, with stability of the other samples being EDTA>Citrate~Heparin>Serum.

Figure 8:
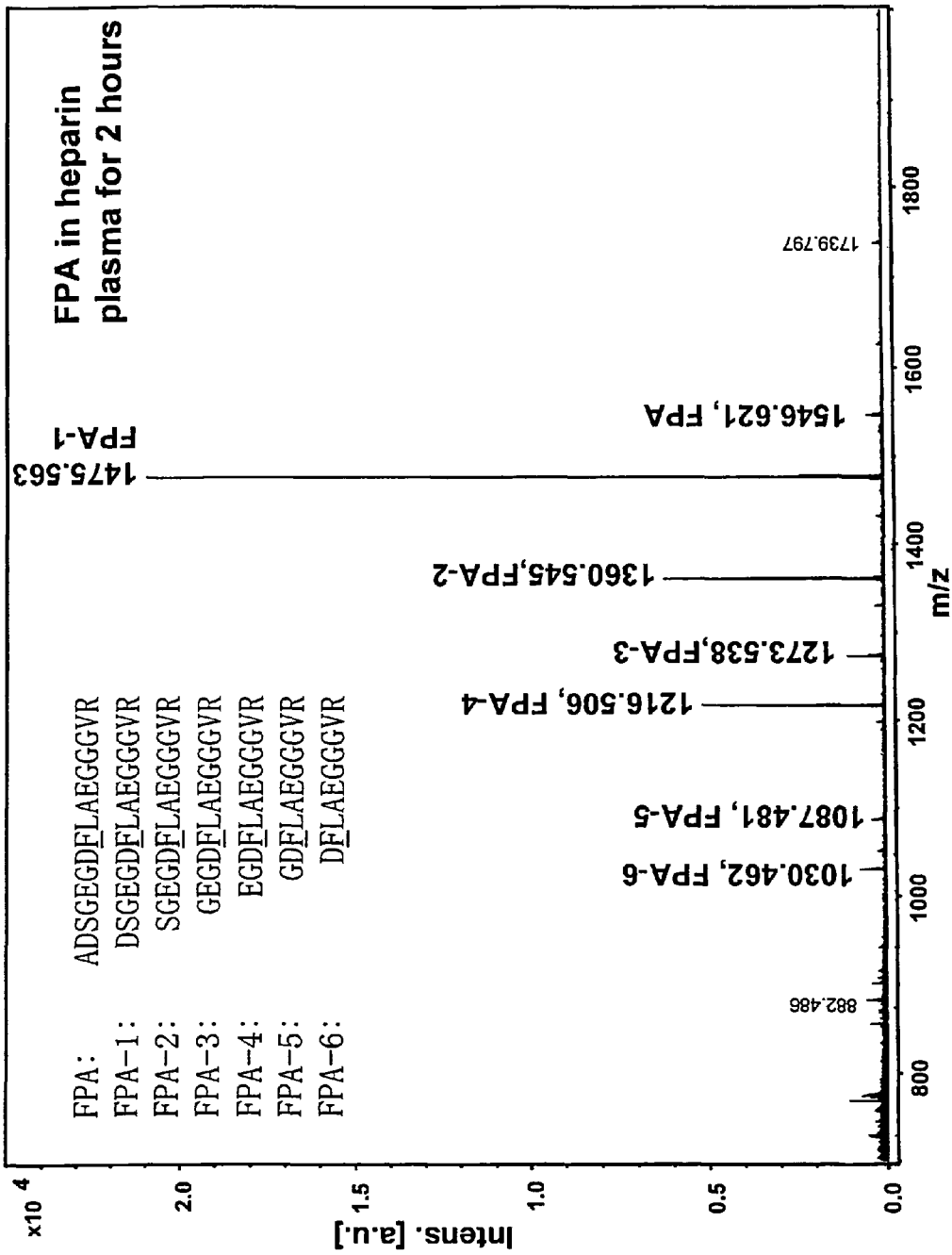
FIG. 8 is a magnified plot of a spectrum of FPA and its fragments in a heparin sample after two hours incubation (SEQ ID NOS 1-7, respectively, in order of appearance).

The observed decrease of the spiked AQUA FPA peptide is caused by the intrinsic amino-peptidase activity (9, 15, 20, 33) as its six fragments, sequentially truncated from the amino terminus, can be detected during the incubation (FIG. 3, FIG. 8). The process was easily observed in heparinized plasma, since the relative instability in this sample facilitated detection of the various truncated peptides within a reasonable experimental time frame (FIG. 3). At "Time 0", which means exposure for only a few seconds of the labeled peptide to the plasma prior to quenching, the two largest truncated ("daughter") peptides (FPA-1, and FPA-2) were detected (FIG. 3), suggesting rapid enzymatic degradation. The starting FPA prior to spiking was measured as a clean, single peptide with expected molecular weight (FIG. 6), and thus even a few seconds of exposure in the heparin plasma was sufficient to demonstrate the degradation of the spiked peptide. During further incubation, smaller daughter peptides were detected: FPA-3 at 30 min, FPA-4 at one hour, and both FPA-5 and FPA-6 at two hours (FIG. 3, FIG. 8). None of these peptides was detected after eight-hour incubation.

Importantly, the abundance of the first four daughter peptides (FPA-1 to FPA-4) displayed a pattern of increased intensity up to about two hours and decreased thereafter (FIG. 3). This increase-then-decrease pattern, depicted in FIG. 4B, indicates that these truncated peptides are intermediates of a sequential (or consecutive) reaction caused by intrinsic plasma amino-peptidase activity.

The measurement of the degradation products was sufficiently unambiguous as to allow definition of a kinetic model of the degradation process. To determine the rate constants of the sequential reaction, the fragments of FPA: FPA-1, FPA-2, FPA-3, FPA-4 (FIG. 3), were measured in heparin plasma pooled from three healthy individuals with four replicates, and the average of peak intensities were modeled according to a first-order SMSR (FIG. 4). Simulation of the peak intensities of time-course MS (FIG. 4B) gave apparent rate constants of the sequential reactions: $k_1=2.1$, $k_2=0.29$, $k_3=1.96$, $k_4=1.6$, and $k_5=0.04$ h$^{-1}$ for the first five step truncations (FIG. 4A), with goodness-of-fit ($R^2$) of 0.84, 0.78, 0.77, 0.87, and 0.76, respectively. Accordingly, the half-lives of FPA, FPA-1, FPA-2, FPA-3, and FPA-4 are 0.29, 2.1, 0.31, 0.38, and 15.2 hours, respectively (FIG. 4A). These data suggest that each peptide has a unique half-life, or a unique liability of the N-terminal residue (A, D, S, G, and E on FPA, FPA-1, FPA-2, FPA-3, and FPA-4, respectively) to further truncation. Two shortened peptides, FPA-1 and FPA-4, both with a negatively charged N-terminal residue, have enhanced half-lives of 7-fold and 52-fold compared to the parental FPA, respectively, while other three neutral N-terminal peptides, FPA, FPA-2, and FPA-3 have relatively similar half-lives. These results suggest that a negative charge on the leaving residue contributes to the stabilization of the peptide, or indicate a significant contribution of the N-terminal residue on sequence-specificity of the peptidase activity. Furthermore, the simulation curves match well with the experimental data (FIG. 4B). This good fitting suggests that the modeling SMSR is applicable to a general exopeptidase-caused sequential reaction.

Peptidase-induced peptide degradation appeared to be fairly ubiquitous, as instability has been observed for all other isotopic labeled peptides tested to date by Applicants, including complement component 4 (C4) and component 3 peptide (C3f) (Table 1), brain natriuretic peptide (BNP), glucagon-like peptide-1 (GLP-1), and bradykinin (data not shown). Both aminopeptidase and carboxypeptidase activities were constantly observed on the spiked peptides, e.g., aminopeptidases truncate the N-terminal residues of FPA and C3f, and carboxypeptidases act on the C-terminal residues of C4 peptides, similar to the observation of these exopeptidase activities acting on the intrinsic peptides (9, 20, 33). The degradation of these spiked peptides fit the observed first-order kinetics, and therefore the half-life of each peptide is, to a large extent, independent of its concentration. Thus, both abundant and rare peptides, whether spiked or naturally existing in the blood samples, may be subjected to peptidase-mediated instability without regard to peptide abundance.

Spiking of distinctly detectable isotope-labeled peptides also gives in vitro controls that cannot be gained otherwise. The fast change in intrinsic peptides makes it virtually impossible to characterize their (in)stability during early sample collection (20). Spiking the uniquely identifiable exogenous control allows us for a true definition of "time zero" for time-dependent studies, as well as to track the spiked peptide and its breakdown products which can be easily distinguished from endogenous peptides by MS-based analysis. Compared with previous works (9, 15, 20, 33) showing "what" happens in terms of peptidase-caused truncations of endogenous peptides, the disclosed kinetics analysis further provides "how" the peptides get cleaved.

As the intrinsic peptidase(s) responsible for these truncations have been not completely identified, multiple peptidases and/or proteases are possibly involved in the digestion of any one peptide. In this case, the observed reaction is possibly the summation of multiple reactions, and the measured rate constant is actually an observed rate constant ($k_{obs}$) of this observed reaction. Yet, the disclosed first-order SMSR model, discussed above, is consistent with a simple Michaelis-Menton kinetics for each step reaction: S (peptide)+E (peptidase)↔SE→P (shorter peptide)+E considering that the assumption of $K_m>>[S]$ and thus, $V=V_{max}[S]/K_m$ or $k=V_{max}/K_m$, is appropriate in this system as the concentration of each parent or daughter peptide is no more than the initial concentration of spiked peptide at 50 fmol/µL, i.e. $5\times10^{-9}$ M, while a blood peptidase is expected to have much higher value of $K_m$, such as, human plasma FXIII ($K_m=1.98\times10^{-5}$ M), 34 and carboxypeptidase N ($K_m=0.25-1.5\times10^{-3}$ M). 35

Two related features of instability with regard to the identity of the peptides have been observed, suggesting substrate specificity of the peptidase activity intrinsic to blood samples. First, while peptidase-mediated instability seems to be universal, different peptides exhibited different half-lives (Table 1), indicating an influence of peptide sequence upon intrinsic instability. Second, and more specifically, half-life differences were observed among the parent and four daughter peptides of FPA family suggesting that peptides with negatively charged amino-terminal residues have better stability (FIG. 4). But the three FPA peptides, FPA, FPA-2, and FPA-3 with neutral N-terminal residues A, S, and G, respectively, showed only a slight, if any, difference in their half-lives with 0.29, 0.31, and 0.38 hours, respectively (FIG. 4A). It is not clear if this difference is due to the slight differences in the peptide size/length or in the three N-terminal residues or both. However, it is reasonable to conclude that plasma and serum peptides, including potentially important and useful peptide biomarkers, vary over time in a sequence-dependent manner, and that these intrinsic peptidase(s)-induced variations follow the observed first-order SMSRs in digestion of peptides (FIGS. 2 & 4).

The primary, full-length FPA ("parental" FPA) generated in serum sample has been reported to be further subjected to ex vivo peptidase digestion into shorter peptides. The pattern of the FPA family of peptides can distinguish myocardial infarction (15), and cancer diseases (9) from controls, thus implying that some disease states can alter intrinsic peptidase activity in blood, and activity measurements may have diagnostic utility. In the current study, simultaneous detection of changes among all of the FPA-derived peptides (FIG. 3), and modeling according to SMSR, revealed that FPA-4 has the longest half-life among this peptide family (FIG. 4), at least in the heparin sample. Different blood sample types led to different relative stabilities. Whether a peptide biomarker is intrinsic to blood in vivo or is generated ex vivo during the sample process, harnessing peptidase activity as the biomarker and performing a careful evaluation of stability as shown here provide useful information for moving a newly discovered peptide successfully through biomarker validation.

There was also strong and obvious influence of the nature of the blood sample itself (serum and various plasmas) upon the degradation process (FIG. 1). The surprising speed of degradation in serum suggested that peptidase activity was stimulated during the clotting processes, further supporting the general observation of plasma being an intrinsically more stable sample than serum. (20,24). Since each type of plasma was mixed with alternative chemicals (EDTA, Citrate, or Heparin) included in the collection tube, the uniquely chemically altered subsets of peptidase activities, leading to the differential stability. Likely, there are several or more different types of peptidases in blood, each being differentially inhibited by typical anticoagulants. Further inclusion of protease inhibitors in an EDTA plasma, facilitated by BD P100 with its formulation providing a broader spectrum of inhibitors against more intrinsic peptidases, provided further stabilization for plasma peptidome studies (FIG. 1 and Table 1), consistent with previous observations that the protease-inhibited plasma provides a more robust sample for proteome study (20).

Stable isotopically labeled peptides are often used as internal standards (or controls) for quantitative proteomics (28-30). Use of these control peptides should also include careful evaluation of their stability, as the instability of the spiked peptides shown here is influenced by the nature of the blood sample itself. The fast speed at which some blood samples (e.g., serum and heparin plasma) degraded both spiked and existing peptides suggests that the desired accurate quantitation by normalization to those labile controls may be compromised. Indeed, the use of such peptides for MS-based absolute quantitation of proteins can lead to severe bias (36). The results disclosed herein suggest that including the protease and peptidase inhibitors in plasma collection enhances the stability not only of the plasma proteins (20), but also for spiked control peptides, and thus presumably the accuracy of absolute quantification using these approaches.

Direct measurement of the degradation of isotopically labeled peptides spiked into a variety of blood sample types shows that the extent of intrinsic peptidase activities encumbers peptide biomarker studies. The use of the spiked peptides provides an in vitro control for time-dependent analysis (FIGS. 1&2), and allows direct measurement of kinetic degradation rate of any targeted peptide and its degradation intermediates (FIGS. 3&4). The results disclosed herein show that intrinsic plasma peptidases digest peptides in a first-order SMSR (FIGS. 2&4), and the rate of degradation varies with both the peptide sequences (Table 1 and FIG. 4) and the nature of the collected sample (FIG. 1 and Table 1), sometimes being so fast that measurement of the full-length spiked peptide may become impossible (e.g., FPA in a serum). While peptidase activity has been widely reported previously, and may provide diagnostic utility (9, 15), both sample variability from time to time, type to type, and the instability of the targeted peptide biomarker need to be accounted for when we are trying to harness the utility of blood peptides as biomarkers. Measurement of the degradation of peptides of interest can aid in refining their diagnostic values. Also, the proteolytic effect of intrinsic plasma peptidase activities on a spiked control peptide when used for quantitation and/or normalization should not be overlooked. Further, inclusion of protease inhibitors can alleviate the peptidase-caused preanalytical variability for better stabilization of both endogenous peptides as biomarkers and spiked peptides as controls.

REFERENCES (1) Anderson, N. L.; Anderson, N. G. The Human Plasma Proteome—History, Character, and Diagnostic Prospects. *Mol. Cell. Proteomics* 2002, 1, 845-867.

(2) Omenn, G. S., States, D. J.; Adamski, M.; Blackwell, T. W.; Menon, R.; Hermjakob, H., et al. Overview of the HUPO Plasma Proteome Project: results from the pilot phase with 35 collaborating laboratories and multiple analytical groups, generating a core dataset of 3020 proteins and a publicly-available database. *Proteomics* 2005, 5, 3226-3245.

(3) Adam, B. L.; Qu, Y.; Davis, J. W.; Ward, M. D.; Clements, M. A.; Cazares, L. H.; Semmes, O. J.; Schellhammer, P. F.; Yasui, Y.; Feng, Z.; Wright, G. L. Jr. Serum protein fingerprinting coupled with a pattern-matching algorithm distinguishes prostate cancer from benign prostate hyperplasia and healthy men. *Cancer Res.* 2002, 62, 3609-3614.

(4) Petricoin, E. F.; Ornstein, D. K.; Liotta, L. A. Clinical proteomics: Applications for prostate cancer biomarker discovery and detection. *Urol. Oncol.* 2001, 22, 322-8.

(5) Ebert, M. P. A.; Ebert, M. P.; Meuer, J.; Wiemer, J. C.; Schulz, H. U.; Reymond, M. A.; Traugott, U.; Malfertheiner, P., Rocken, C. Identification of gastric cancer patients by serum protein profiling. *J. Proteome Res.* 2004, 3, 1261-1266.

(6) Mor, G., Visintin, I., Lai, Y., Zhao, H., Schwartz, P., Rutherford, T., Yue, L., Bray-Ward, P., Ward, D. C. Serum protein markers for early detection of ovarian cancer. *Proc. Natl. Acad. Sci. USA* 2005, 102, 7677-7682.

(7) Irizarry, M. C. Biomarkers of Alzheimer disease in plasma. *NeuroRx* 2004, 1, 226-234.

(8) Petricoin, E. F.; Ardekani, A. M.; Hilt, B. A.; Levin, P. J.; Fusaro, V. A.; Steinberg, S. M.; Mills, G. B.; Simone, C.; Fishman, D. A.; Kohn, E. C.; Lotta, L. A. Use of proteomic patterns in serum to identify ovarian cancer. *Lancet* 2002, 359, 572-577.

(9) Villanueva, J.; Shaffer, D. R.; Philip, J.; Chaparro, C. A.; Erdjument-Bromage, H.; Olshen, A. B.; Fleisher, M.; Lilja, H.; Brogi, E.; Boyd, J.; Sanchez-Carbayo, M.; Holland, E. C.; Cordon-Cardo, C.; Scher, H. I.; Tempst, P. Differential exoprotease activities confer tumor-specific serum peptidome patterns. *J. Clin. Invest.* 2006, 116, 271-284.

(10) Moe, G. W. B-type natriuretic peptide in heart failure *Curr. Opin. Cardiol.* 2006, 21, 208-214.

(11) Theodorescu, D.; Wittke, S.; Ross, M. M.; Walden, M.; Conaway, M.; Just, I.; Mischak, H.; and Frierson, H. F. Discovery and validation of new protein biomarkers for urothelial cancer: a prospective analysis. *Lancet Oncol.* 2006, 7, 230-240.

(12) Ogata, Y.; Heppelmann, C. J.; Charlesworth, M. C.; Madden, B. J.; Miller, M. N.; Kalli, K. R.; Cilby, W. A.; Robert Bergen, H. 3rd; Saggese, D. A., and Muddiman, D. C. Elevated levels of phosphorylated fibrinogen-alpha-isoforms and differential expression of other post-translationally modified proteins in the plasma of ovarian cancer patients. *J. Proteome Res.* 2006, 5, 3318-25.

(13) Ebert, M. P. A.; Niemeyer, D.; Deininger, S. O.; Wrx, T.; Knipping, C.; Hoffmannn, J.; Sauer, J.; Albrecht, W.; Malfertheiner, P.; Rochen, C. Identification and confirmation of increased fibrinopeptide a serum protein levels in gastric cancer sera by magnet bead assisted MALDI-TOF mass spectrometry. *J. Proteome Res.* 2006, 5, 2152-2158.

(14) Orvisky, E.; Drake, S. K.; Martin, B. M.; Abdel-Hamid, M.; Ressom, H. W.; Varghese, R. S.; An, Y.; Saha, D.; Hortin, G. L.; Loffredo, C. A., and Goldman, R. Enrichment of low molecular weight fraction of serum for MS analysis of peptides associated with hepatocellular carcinoma. *Proteomics* 2006, 6, 2895-902.

(15) Marshall, J.; Kupchak, P.; Zhu, W.; Yantha, J.; Vrees, T.; Furesz, S.; Jacks, K.; Smith, C.; Kireeva, I.; Zhang, R.; Takahashi, M.; Stanton, E.; Jackowski, G. Processing of serum proteins underlies the mass spectral fingerprinting of myocardial infarction. *J. Proteome Res.* 2003, 2, 361-72.

(16) Aebersold, R.; Anderson, L.; Caprioli, R.; Druker, B.; Hartwell, L.; Smith, R. Perspective: A Program to improve protein Biomarker Discovery for Cancer. *J. Proteome Res.* 2005, 4, 1104-1109.

(17) Coombes, K. R.; Morris, J. S.; Hu, J.; Edmonson, S. R., Baggerly, K. A. Serum proteomics profiling—a young technology begins to mature. *Nat. Biotechnol.* 2005, 23, 291-292.

(18) Check, E. Proteomics and cancer: running before we can walk? *Nature* 2004, 429, 496-97.

(19) Diamandis, E. P. Peptidomics for cancer diagnosis: present and future. *J. Proteome Res.* 2006, 5, 2079-82.

(20) Yi, J.; Kim, C.; Gelfand, C. A. Inhibition of intrinsic proteolytic activities moderates preanalytical variability and instability of human plasma. *J. Proteome Res.* 2007, 6, 1768-1781.

(21) Flaig, T. W.; Nordeen, S. K.; Lucia, M. S.; Harrison, G. S., and Glode, L. M. Conference report and review: current status of biomarkers potentially associated with prostate cancer outcomes. *J. Urol.* 2007, 177, 1229-1237.

(22) Tammen, H.; Zucht, H. D., and Budde, P. Oncopeptidomics—a commentary on opportunities and limitations. *Cancer Lett.* 2007, 249, 80-86.

(23) Lee, J. W.; Figeys, D.; and Vasilescu, J. Biomarker assay translation from discovery to clinical studies in cancer drug development: quantification of emerging protein biomarkers. *Adv. Cancer Res.* 2007, 96, 269-298.

(24) Rai, A. J.; Gelfand, C. A.; Haywood, B. C.; Warunek, D. J.; Yi, J.; Schuchard, M. D.; Mehigh, R. J.; Cockrill, S. L.; Scott, G. B.; Tammen, H.; Schulz-Knappe, P.; Speicher, D. W.; Vitzthum, F.; Haab, B. B.; Siest, G.; Chan, D. W. HUPO Plasma Proteome Project specimen collection and handling: towards the standardization of parameters for plasma proteome samples. *Proteomics* 2005, 5, 3262-3277.

(25) Banks, R. E.; Stanley, A.; Cairns, D. A.; Barrett, J. H.; Clarke, P.; Thompson, D.; Selby, P. Influences of blood sample processing on low-molecular-weight proteome identified by surface-enhanced laser desorption/ionization mass spectrometry. *Clinical Chem.* 2005, 51, 1637-49.

(26) Hsieh, S. Y.; Chen, R. K.; Pan, Y. H.; Lee, H. L. Systematical evaluation of the effects of sample collection procedures on low-molecular-weight serum/plasma proteome profiling. *Proteomics* 2006, 6, 3189-3198.

(27) Walsh, P. N. & Ahmad, S. S. Proteases in blood clotting. *Essays in Biochemistry* 2002, 38, 95-111.

(28) Gerber, S.; Rush, J.; Stemman, O.; Kirchnet, M. W.; Gygi, S. P. Absolute Quantification of Proteins and Phosphoproteins from cell lysates by tandem MS. *PNAS* 2003, 100, 6940-6945.

(29) Kirkpatrick, D. S.; Gerber, S. A., and Gygi, S. P. The absolute quantification strategy: a general procedure for the quantification of proteins and posttranslational modifications. *Methods* 2005, 35, 265-273.

(30) Mayya, V.; Rozual, K.; Wu, L.; Fong, M. B.; Han, D. K. Absolute Quantification of Multisite phosphorylation by selective Reaction Monitoring Mass Spectrometry. *Mol. Cell. Proteomics* 2005, 5, 1146-1157.

(31) Zhang, X.; Leung, S. M.; Morris, C. R.; Shigenage, M. K. Evaluation or a novel, integrated approach using functionalized magnetic beads, bench-top MALDI-TOF MA with prestructured sample supports, and pattern recognition software for profiling potential biomarkers in human plasma. *J. Biomol. Tech.* 2004, 15, 167-175.

(32) Tholey, A.; Zabet-Moghaddam, M., and Heinzle, E. Quantification of peptides for the monitoring of protease-catalyzed reactions by Matrix-Assisted Laser Desorption/Ionization Mass Spectrometry using ionic liquid matrixes. *Anal. Chem.* 2006, 78, 291-297.

(33) Koomen, J. M.; Li, D.; Xiao, L. C.; Liu, T. C.; Coombes K. R.; Abbruzzese, J.; Kobayashi, R. Direct tandem mass spectrometry reveals limitations in protein profiling experiments for plasma biomarker discovery. *J. Proteome Res.* 2005, 4, 972-981.

(34) Oertel, K.; Hunfeld, A.; Specker, E.; Reiff, C.; Seitz, R.; Pasternack, R.; Dodt, J. A. Highly sensitive fluorometric assay for determination of human coagulation factor XIII in plasma. *Anal. Biochem.* 2007, 367, 152-8.

(35) Willemse, J. L.; Polla, M.; Hendriks, D. F. The intrinsic enzymatic activity of plasma procarboxypeptidase U (TAFI) can interfere with plasma carboxypeptidase N assays. *Anal. Biochem.* 2006, 356, 157-9.

(36) Brun, V.; Dupuis, A.; Adrait, A.; Marcellin, M.; Thomas, D.; Court, M.; Vandenesch, F.; Garin, J. Isotope-labeled protein standards: toward absolute quantitative proteomics. *Mol. Cell. Proteomics* 2007, 6, 2139-49.

All publications cited in the specification, both patent publications and non-patent publications are indicative of the level of skill of those skilled in the art to which this invention pertains. Any publication not already incorporated by reference herein is herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of diagnosing a disease condition, comprising:
   a) selecting a protein known or suspected to be a diagnostic marker for the disease condition;
   b) analyzing degradation of the protein in a collected biological sample, comprising identifying degradation product(s) of the protein in the collected sample as a function of time and half-life of the protein and the degradation product(s) of the protein after sample collection;
   c) selecting the protein or the degradation product that exhibits a prior identified measurable half-life at a predetermined period of time, and which is appropriately matched to handling conditions of the sample during the predetermined time period;
   d) measuring presence or amount of the protein or degradation product selected in c) in a collected blood sample as the diagnostic marker for the disease condition; and
   e) correlating said measuring with the presence, absence, or severity of the disease condition.

2. The method of claim 1, wherein the biological sample is collected in a collection vehicle.

3. The method of claim 2, wherein the same type of collection vehicle used in diagnosing the disease condition is used in the prior identification.

4. The method of claim 2, wherein the collection vehicle is a swab.

5. The method of claim 2, wherein the collection vehicle is a container.

6. The method of claim 1, wherein the biological sample is blood or derived from blood.

7. The method of claim 6, wherein the biological sample is blood.

8. The method of claim 2, wherein said collection vehicle comprises a blood collection tube having a clot affecting chemistry.

9. The method of claim 8, wherein the clot-affecting chemistry includes an anti-coagulant.

10. The method of claim 9, wherein the anti-coagulant comprises EDTA.

11. The method of claim 8, wherein the clot-affecting chemistry includes a clot activator or accelerator.

12. The method of claim 8, wherein the blood collection tube is chosen from the group consisting of a serum tube, as serum tube with density separator, a citrate tube, a heparin tube, an EDTA tube, an EGTA tube, a CTAD tube, and a sodium fluoride tube.

13. The method of claim 1, wherein the protein or degradation product thereof selected in c) for the measuring in d) has the greatest half-life.

14. The method of claim 1 where the predetermined time period encompasses a period of at least 2 hours.

15. The method of claim 1 where the predetermined time period encompasses a period between 4 and 27 hours.

16. The method of claim 1 where the handling conditions include subjecting the sample to room temperature.

17. The method of claim 1 wherein the handling conditions include subjecting the sample to freezing or cryopreservation conditions.

18. The method of claim 17 wherein the sample is subjected to freezing.

19. The method of claim 17 wherein the sample becomes cryopreserved.

20. The method of claim 2, further comprising transferring the sample to a second collection vehicle, at some point after sample acquisition and before performing the diagnostic measurement.

21. The method of claim 1, further comprising communicating the presence, absence, or severity of the disease condition.

22. The method of claim 21, wherein said communicating comprises displaying the disease state in a medium selected from the group consisting of an electronic screen, a digital screen, a printable substrate, and an audible signal.

23. A method of identifying a protein or degradation product thereof as a marker for a disease condition, comprising:
  selecting a protein known or suspected to be a diagnostic marker for the disease condition;
  analyzing degradation of the protein in the collected biological sample, comprising identifying degradation product(s) of the protein as a function of time and half-life of the protein and the degradation product(s) after sample collection; and
  selecting the protein or the degradation product that exhibits a prior identified measurable half-life at a predetermined period of time, and which is appropriately matched to handling conditions of the sample during the predetermined time period.

* * * * *